US010646621B2

(12) United States Patent
Doyle et al.

(10) Patent No.: US 10,646,621 B2
(45) Date of Patent: May 12, 2020

(54) MOLECULAR IMPRINTED BIOFUNCTIONAL DEVICE

(71) Applicant: Utah Valley University, Orem, UT (US)

(72) Inventors: Timothy Edwin Doyle, Orem, UT (US); Natalie Charlotte Sullivan, Orem, UT (US)

(73) Assignee: Utah Valley University Foundation, Inc., Orem, UT (US)

( * ) Notice: Subject to any disclaimer, the term of this patent is extended or adjusted under 35 U.S.C. 154(b) by 289 days.

(21) Appl. No.: 15/132,080

(22) Filed: Apr. 18, 2016

(65) Prior Publication Data

US 2016/0303293 A1 Oct. 20, 2016

Related U.S. Application Data

(60) Provisional application No. 62/148,880, filed on Apr. 17, 2015.

(51) Int. Cl.
*A61L 31/10* (2006.01)
*A61N 1/05* (2006.01)
(Continued)

(52) U.S. Cl.
CPC ............ *A61L 31/10* (2013.01); *A61B 5/0478* (2013.01); *A61B 5/1473* (2013.01);
(Continued)

(58) Field of Classification Search
CPC ....... A61L 31/10; A61L 31/16; A61B 5/0478; A61B 5/1473; A61B 10/0233;
(Continued)

(56) References Cited

U.S. PATENT DOCUMENTS 6,131,580 A * 10/2000 Ratner ................ A61F 2/30767
128/898
2003/0236552 A1* 12/2003 Roby ............... A61B 17/06066
606/223

(Continued)

OTHER PUBLICATIONS

Francoise Dignat-George et al., "The Many Faces of Endothelial Microparticles", Arteriosclerosis Thrombosis, and Vascular Biology, Journal of the American Heart Association, atvb.ahajournals. org, Jan. 2011, pp. 27-33.

(Continued)

*Primary Examiner* — Dah-Wei D. Yuan
*Assistant Examiner* — Andrew J Bowman
(74) *Attorney, Agent, or Firm* — Kunzler Bean & Adamson

(57) ABSTRACT

An apparatus is disclosed for a biofunctional molecular imprint apparatus comprising a supportive structure that cuts, punctures, retains, repairs, protects, interrogates, and/ or supports the function of a body tissue or other substance; a surface material that receives and retains a molecular imprint and that is positioned to contact the body tissue or other substance during use; and a molecular imprint of a bioactive molecule that influences blood coagulation, tissue damage, pain, immune response, inflammation, infection, healing, tissue regeneration, cell adhesion, the formation of extracellular matrix, tumorigenesis, angiogenesis, bacterial growth, and/or side effects.

17 Claims, 15 Drawing Sheets

(51) Int. Cl.
| | |
|---|---|
| A61B 5/1473 | (2006.01) |
| A61B 10/02 | (2006.01) |
| A61B 5/0478 | (2006.01) |
| A61F 2/04 | (2013.01) |
| A61F 2/38 | (2006.01) |
| A61F 13/00 | (2006.01) |
| A61L 31/16 | (2006.01) |
| A61M 25/00 | (2006.01) |
| A61N 1/362 | (2006.01) |
| C23C 14/22 | (2006.01) |
| A61B 17/00 | (2006.01) |
| A61B 5/1486 | (2006.01) |
| A61F 2/30 | (2006.01) |
| A61B 17/14 | (2006.01) |
| A61B 17/16 | (2006.01) |
| A61B 17/28 | (2006.01) |
| A61B 17/3201 | (2006.01) |
| A61B 17/3211 | (2006.01) |
| A61M 5/142 | (2006.01) |
| A61M 5/32 | (2006.01) |

(52) U.S. Cl.
CPC .......... *A61B 10/0233* (2013.01); *A61F 2/04* (2013.01); *A61F 2/38* (2013.01); *A61F 13/00063* (2013.01); *A61L 31/16* (2013.01); *A61M 25/0043* (2013.01); *A61N 1/0534* (2013.01); *A61N 1/0536* (2013.01); *A61N 1/362* (2013.01); *C23C 14/22* (2013.01); *A61B 5/14865* (2013.01); *A61B 10/0275* (2013.01); *A61B 17/14* (2013.01); *A61B 17/1615* (2013.01); *A61B 17/28* (2013.01); *A61B 17/3201* (2013.01); *A61B 17/3211* (2013.01); *A61B 2017/00022* (2013.01); *A61B 2017/00039* (2013.01); *A61B 2017/00526* (2013.01); *A61B 2017/00884* (2013.01); *A61B 2017/00889* (2013.01); *A61B 2017/00893* (2013.01); *A61B 2017/00938* (2013.01); *A61B 2017/00942* (2013.01); *A61B 2562/0285* (2013.01); *A61F 2002/30677* (2013.01); *A61L 2300/252* (2013.01); *A61L 2300/418* (2013.01); *A61L 2400/18* (2013.01); *A61L 2420/02* (2013.01); *A61M 5/14248* (2013.01); *A61M 5/32* (2013.01); *A61M 2025/0057* (2013.01); *A61M 2205/0244* (2013.01); *A61M 2207/10* (2013.01)

(58) Field of Classification Search
CPC ..... A61B 17/14; A61B 17/1615; A61B 17/28; A61B 17/3201; A61B 17/3211; A61F 2/04; A61F 2/38; A61F 13/00063; A61M 25/0043; A61N 1/0534; A61N 1/0536; A61N 1/362
See application file for complete search history.

(56) References Cited

U.S. PATENT DOCUMENTS

| | | | |
|---|---|---|---|
| 2008/0142366 A1* | 6/2008 | Tamirisa | C25D 13/04 204/456 |
| 2009/0143806 A1 | 6/2009 | Witt et al. | |
| 2009/0318788 A1 | 12/2009 | Levon et al. | |
| 2010/0015201 A1 | 1/2010 | Borck et al. | |
| 2010/0305688 A1 | 12/2010 | Cantrell et al. | |
| 2012/0123235 A1 | 5/2012 | Borck et al. | |
| 2012/0150015 A1 | 6/2012 | Sandhu et al. | |
| 2012/0150286 A1 | 6/2012 | Weber et al. | |
| 2012/0197180 A1* | 8/2012 | Minteer | A61K 9/0009 604/20 |
| 2012/0209090 A1* | 8/2012 | Goodall | A61B 5/0071 600/309 |
| 2012/0238835 A1* | 9/2012 | Hyde | A61B 5/14507 600/302 |
| 2014/0134240 A1* | 5/2014 | Kaplan | A61L 27/227 424/451 |

OTHER PUBLICATIONS

Toru Shiomi et al., "A Method for the Molecular Imprinting of Hemoglobin on Silica Surfaces Using Silanes", Science Direct, Biomaterials 26, www.sciencedirect.com, Apr. 2005, pp. 5564-5571.
Jonathan C. Claussen et al., "Probing the Enzymatic Activity of Alkaline Phosphatase Within Quantum Dot Bioconjugates", The Journal of Physical Chemistry, Selected Works, http://works.bepress.com/jonathan_claussen/12, Jan. 2015, pp. 2208-2221.
Lawrence F. Brass, "Thrombin and Platelet Activation", Chest Journal vol. 124, No. 3, www.chestjournal.org, Sep. 2003, pp. 18S-25S.
Richard J. Ansell et al., "Imprinted polymers for chiral resolution of (±)-ephedrine. Part 3:† NMR predictions and HPLC results with alternative functional monomers", The Royal Society of Chemistry 2009, www.rsc.org/analyst, Nov. 28, 2008, pp. 564-576.
Daniel C Leslie et al., "A bioinspired omniphobic surface coating on medical devices prevents thrombosis and biofouling", Nature Biotechnology, vol. 32, No. 11, Nov. 2014, pp. 1134-1140 and 3 additional pages.
Shima Taheri et al., "Substrate independent silver nanoparticle based antibacterial coatings", ScienceDirect, Biomatericals 35, www.sciencedirect.com, Mar. 12, 2014, pp. 4601-4609.
Phong A Tran et al., "Antimicrobial selenium nanoparticle coatings on polymeric medical devices" IOPScience, iopscience.iop.org, Nanotechnology 24, Mar. 22, 2014, 7 pages.
Tran et al., "Antimicrobial Selenium Nanoparticle Coatings on Polymeric Medical Devices", IP Publishing, Nanotechnology, No. 24, Mar. 22, 2013, pp. 1-7.
Leslie et al., "A Bioinspired Omniphobic Surface Coating on Medical Devices Prevents Thrombosis and Biofouling", Nature Biotechnology, vol. 32, No. 11, Nov. 2014, pp. 1134-1140.
Jy et al., "Endothelial Microparaticles Induce Formation of Platelet Aggregates via a von Willebrand Factor/Ristocetin Dependent Pathway, Rendering them Resistant to Dissociation", Journal of Thrombosis and Haemostasis, No. 3, Feb. 21, 2005, pp. 1301-1308.
Dignat-George et al., "The Many Faces of Endothelial Microparticles", Arterioscler Thrombosis, and Vascular Biology, Journal of the American Heart Association, http://atvb.ahajournals.org, Jan. 2011, pp. 27-33.
Ansell et al., "Imprinted Polymers for Chiral Resolution of (±)-Ephedrine. Part 3:† NMR Predictions and HPLC Results with Alternative Functional Monomers‡", The Royal Society of Chemistry, www.rsc.org/analyst, Nov. 2008, pp. 564-576.
Shiomi et al., "A Method for the Molecular Imprinting of Hemoglobin on Silica Surfaces using Silanes", Science Direct, www.sciencedirect.com, Apr. 7, 2005, pp. 5564-5571.
Claussen "Probing the Enzymatic Activity of Alkaline Phosphatase Within Quantum Dot Bioconjugates", The Journal of Physical Chemistry, SelectedWorks of Jonathan C. Claussen, http://works.bepress.com/jonathan_claussen/12, Jan. 2015, pp. 2208-2221.
Lee et al., "Small Molecule Inhibitors of PSD95-nNOS Protein-Protein Interactions as Novel Analgesics", Science Direct, Neuropharmacology, www.elsevier.com/locate/neuropharm, Jun. 2015, pp. 464-475.
Taheri et al., "Substrate Independent Silver Nanoparticle Based Antibacterial Coatings", Science Direct, Biomaterials, www.elsevier.com/locate/biomaterials, Mar. 2014, pp. 4601-4609.
Brass, "Thrombin and Platelet Activation", Thrombin: Physiology and Pathophysiology, www.chestjournal.org, vol. 124, No. 3, Sep. 2003, pp. 18S-25S.

(56) References Cited

OTHER PUBLICATIONS

Butenas et al., "Tissue Factor Activity and Function in Blood Coagulation", Thromboisi Research, 122 supplement, 2008, pp. S42-S46.
PCT/US2016/028163, Notification of Transmittal of the International Search Report and the Written Opinion of the International Searching Authority, or the Declaration, dated Sep. 15, 2016.

* cited by examiner

300

400

1100

MOLECULAR IMPRINTED BIOFUNCTIONAL DEVICE

CROSS-REFERENCES TO RELATED APPLICATIONS

This application claims the benefit of U.S. Provisional Patent Application No. 62/148,880 entitled "Molecular Imprinted Biofunctional Device" and filed on Apr. 17, 2015 for Timothy Edwin Doyle, which is incorporated herein by reference.

FIELD OF THE INVENTION

This invention relates to a biofunctional device and more particularly relates to a molecular imprinted biofunctional device.

BACKGROUND

To date, surgery has been performed with instruments using inorganic materials (mineral- and metal-based) and physical effects to function. Initially the scalpel was used solely to make incisions in tissue. The composition of these scalpels has historically followed the trend of blades composed of flint, bronze, iron, and finally stainless steel. Current scalpels use inert materials such as stainless steel to cut tissue, or use energy from electrical, laser, or ultrasonic fields to simultaneously cut and cauterize the tissue. The steel scalpel has the disadvantage of bleeding from the incision, whereas cauterization methods destroy tissue to mitigate bleeding. Likewise, other current medical devices and implants use inert materials.

Limiting blood loss during surgery is a universal patient need that is essential for maintaining normal perioperative tissue and organ function and optimizing post-operative recovery. Consequently, the scalpel was reconfigured to simultaneously cut tissue and reduce bleeding. Some scalpels use heat to cut and cauterize tissue, and thus induce protein denaturation, which leads to fusion of intimal layers of blood vessels. Such scalpels employ physical fields such as electrical (ohmic heating), magnetic, electromagnetic, laser (light absorption), or ultrasonic (thermoviscous effects). Heat scalpels also include electrosurgery, harmonics, and $CO_2$ lasers. Each of these heating techniques causes thermal denaturation of blood proteins that are known to enhance hemostasis but also damage tissue and nerves.

Electrosurgery heats the scalpel blade by direct or alternating current passing through a resistive metal wire electrode into the patient's body and back to the generator though a receiving electrode adhesive pad. The pad is typically applied to the distal portion of the patient's leg. Electrosurgery can result in an unintended burn if the electrical current leaks to any conductive element, or if the electrode cable comes in contact with the patient's body. At lower frequencies, the electrical current can also depolarize cell membranes, and can cause neuromuscular excitation, pain, and even cardiac arrhythmia. However, at high frequencies, the current is less able to affect ions within the tissue cells, making neuromuscular effects negligible. In comparison to other methods, tissue heating from electrosurgery is more localized, which may reduce adverse effects on the tissue.

In the last 20 years the design of $CO_2$ lasers has improved due to the introduction of a new hollow tube delivery system that is currently favored for its limited damage of adjacent tissue. In comparison to harmonic scalpels, which use mechanical ultrasonic vibrations to coagulate blood and cauterize tissue, $CO_2$ lasers can cauterize vessels as small as 0.5 mm in diameter. $CO_2$ lasers and electrosurgery devices may perform with statistically significant speed, on incision and excision, compared to traditional cold knife scalpels and additionally produce less tissue damage. However, scientists disagree on which scalpel is less damaging to tissue and nerves. Some studies have shown that electrosurgery and harmonic scalpels are equally damaging to nerves. Results were based on incisions at three different distances from the nerve: 1 mm, 3 mm, and 5 mm. When tissue was cut adjacent to a nerve, the closer to the nerve, the more nerve damage occurred. However, according to these results, the differences between these devices are negligible. They all burn tissue. High temperatures cause rapid explosive vaporization of water content within tissue, causing fragmentation and drying. Heat effects of $CO_2$ laser and electrocautery scalpels may also be associated with deeper staining, distorted nuclei, and thrombosed or collapsed blood vessels and lymphatics in comparison to traditional cold knife scalpels. In addition, tissue adjacent to the electrode is subject to tissue fragmentation. Though each may have its own distinct advantages for the practitioner including costs, due to the consequences of using heat, each type of scalpel has similar results in terms of the consequences for the patient. Thus, a better instrument is needed to avoid adverse effects to the patient.

A second technique for reducing bleeding in surgery is through topical hemostatic agents. Hemostatic agents come in a variety forms including liquid, foam, sponge, mesh and powder that can be applied by the surgeon at the site of incision. These types of topical agents are made from human pooled proteins, including thrombin and fibrin. Topical agents initiate the blood clotting and coagulation cascade; however they can have side effects due to their active ingredients. Topical agents such as INSTAT [Ethicon], GELFOAM [Pfizer] and SURGICEL [Ethicon] can respectively cause allergic reactions, infection, adhesions, and foreign body reactions. Additionally, particularly for larger vessels this method is not effective alone. Pressure must be applied to large vessels before using this method. Thus, alternative blood loss prevention methods could decrease the associated risks of foreign blood products.

While these current methods are effective for lessening blood loss as compared to cold knife scalpels, there has been little investigation into creating catalytic binding sites on the scalpel surface to catalyze the body's natural coagulation as an alternative to the damaging effects of heat. Thus, a need exists for a less damaging cutting device than those currently known in the art. Beneficially, such a device may also control bleeding, minimize pain, discourage infection, promote healing, and/or provide other benefits.

Some medical devices reside temporarily or permanently in the body of a patient. These devices include catheters and implantable medical devices (artificial organs, cardiac-assist devices, artificial joints, deep brain stimulation or DBS, etc.). Beneficially, a surface material for these devices could minimize microbial growth and blood clotting and also maximize biocompatibility to minimize the body's immune response to the implant and yet allow healing and/or provide other benefits.

Current approaches for catheters and implantable devices include attaching molecules to the surface to create a molecule-thick coating. For example, perfluorocarbon has been used as a molecular coating to create a universally repellant surface for blood clots and biofilms. Additional technologies coat device surfaces with gold, silver, and selenium nanoparticles to give them antimicrobial properties. However, current device surface coating technologies often cannot incorporate all desirable aspects, such as antimicrobial and immunosuppressant action and promotion of healing. Thus, a need exists for a device incorporating the action of a mixture of molecules with multiple complementary functions benign to the body's own responses.

SUMMARY

From the foregoing discussion, it should be apparent that a need exists for a biofunctional medical apparatus that would minimize damage from cutting, clamping, and puncture in medical procedures. Beneficially, such an apparatus would control bleeding, minimize pain, discourage infection, promote healing and/or provide other benefits. It should further be apparent that a need exists for an implantable biofunctional apparatus that would minimize microbial growth and blood clotting. Beneficially, such an apparatus would maximize biocompatibility to minimize the body's immune response to the implant and yet allow healing and/or provide other benefits.

The present invention has been developed in response to the present state of the art, and in particular, in response to the problems and needs in the art that have not yet been fully solved by currently available medical devices. Accordingly, the present invention has been developed to provide a biofunctional apparatus for surgery and implantation devices that overcomes many or all of the above-discussed shortcomings in the art.

Herein provided is a biofunctional molecular imprint apparatus comprising a supportive structure that cuts, punctures, retains, repairs, protects, interrogates, and/or supports the function of a body tissue or other substance, a surface material that receives and retains a molecular imprint and that is positioned to contact the body tissue or other substance during use, and a molecular imprint of a bioactive molecule that influences blood coagulation, tissue damage, pain, immune response, inflammation, infection, healing, tissue regeneration, cell adhesion, the formation of extracellular matrix, tumorigenesis, angiogenesis, bacterial growth, and/or side effects. In some embodiments the surface material comprises a polymer film. In various embodiments the bioactive molecule comprises fibrinogen, fibronectin, PAR 1, PAR 4, ephedrine, a VEGF inhibitor, and/or an HER2-inhibitor.

The supportive structure sometimes comprises titanium, stainless steel, ceramic, plastic, carbon polyethylene, cobalt chromium alloys, ceramic, tantalum, zirconium alloy, oxinium alloy, and/or other material. In certain embodiments the apparatus comprises a medical device.

The medical device may comprise a scalpel, a scissor, a needle, a clamp, a bandage, a cutting tool, a forceps, a drill, a bone saw, a catheter, a skeletal implant, an artificial organ, a pacemaker, an insulin pump, or an intracranial brain electrode. The needle sometimes comprises a hypodermic needle, a biopsy needle, or an intravenous needle. The medical device sometimes comprises a skeletal implant, which may be an artificial joint or other device. The scalpel surface material may comprise a plurality of zones that contact the tissue at different stages of cutting and the molecular imprint may comprise one or more distinct molecules, which are sometimes arrayed within the zones. In some embodiments the shape of the scalpel and/or the molecular imprint is designed for use in a specific type of surgery and/or the treatment of a specific disease. The molecular imprint is sometimes customized to a specific patient or set of patients In some embodiments the supportive structure and/or the surface material of the scalpel comprises a semiconductor, a nanoparticle quantum dot, nano-island and/or a wire. In certain embodiments the supportive structure and/or the surface material comprises a biosensor comprising an interdigital electrode or another device. In certain embodiments the nanoparticle quantum dot, nano-island and/or wire produces an electron wave function configuration that dynamically reconfigures the electron charge distribution within the molecular imprint, enabling tuning of the molecular imprint.

Sometimes an insulating material separates the supportive structure from the polymer film and the molecular imprints. In some embodiments the scalpel comprises a piezoelectric element and/or a semiconductor that generates ultrasonic and/or light waves. The various embodiments the scalpel comprises an acoustic waveguide, an optical fiber, ultrasonic transducer, and/or a laser that may mechanically agitate a protein molecule and induces its separation from the molecular imprint.

Further provided herein is a molecular imprint knife wherein the molecular imprint inhibits the transfer of pathogens on the knife surfaces, and/or senses the presence of pathogen biomarkers. Also provided is a cutting tool wherein during the cutting process the molecular imprint enhances the cross-link density of a soft polymer on a cut surface, changes the polarity of the cut surface to render the surface hydrophobic or hydrophilic, and/or otherwise alters the cut surface.

Additionally provided herein is an embodiment of a method for a biofunctional molecular imprint apparatus comprising molecularly imprinting a set of diverse proteins onto a scalpel blade in a specific spatial pattern to replicate the blood coagulation cascade and/or other biological process as the scalpel blade slices tissue The method herein may comprise imprinting the region closest to a blade edge with molecules that initiate the cascade pathway through vasoconstriction and platelet adhesion. In some embodiments these molecules comprise endothelin, associated enzymes, thromboxane A2, and/or Von Willebrand factor. In certain embodiments of the method herein a region further from the blade edge is imprinted with molecules that aid in the extrinsic pathway. These may comprise thromboplastin, lipoprotein, and/or other molecules. The disclosed method sometimes comprises imprinting a region further from the blade edge with molecules that accelerate the common pathway. In certain embodiments these comprise at factors IX and IXa from the intrinsic pathway, factors VIII and VIIIa, factors V and Va, and/or the like. The method herein sometimes comprises imprinting a region further from the blade edge with molecules that direct activation of thrombin. These molecules may comprise PAR-1, PAR-4, GP Ib-alpha, prothrombin and/or the like.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Introduction

Figure 1:
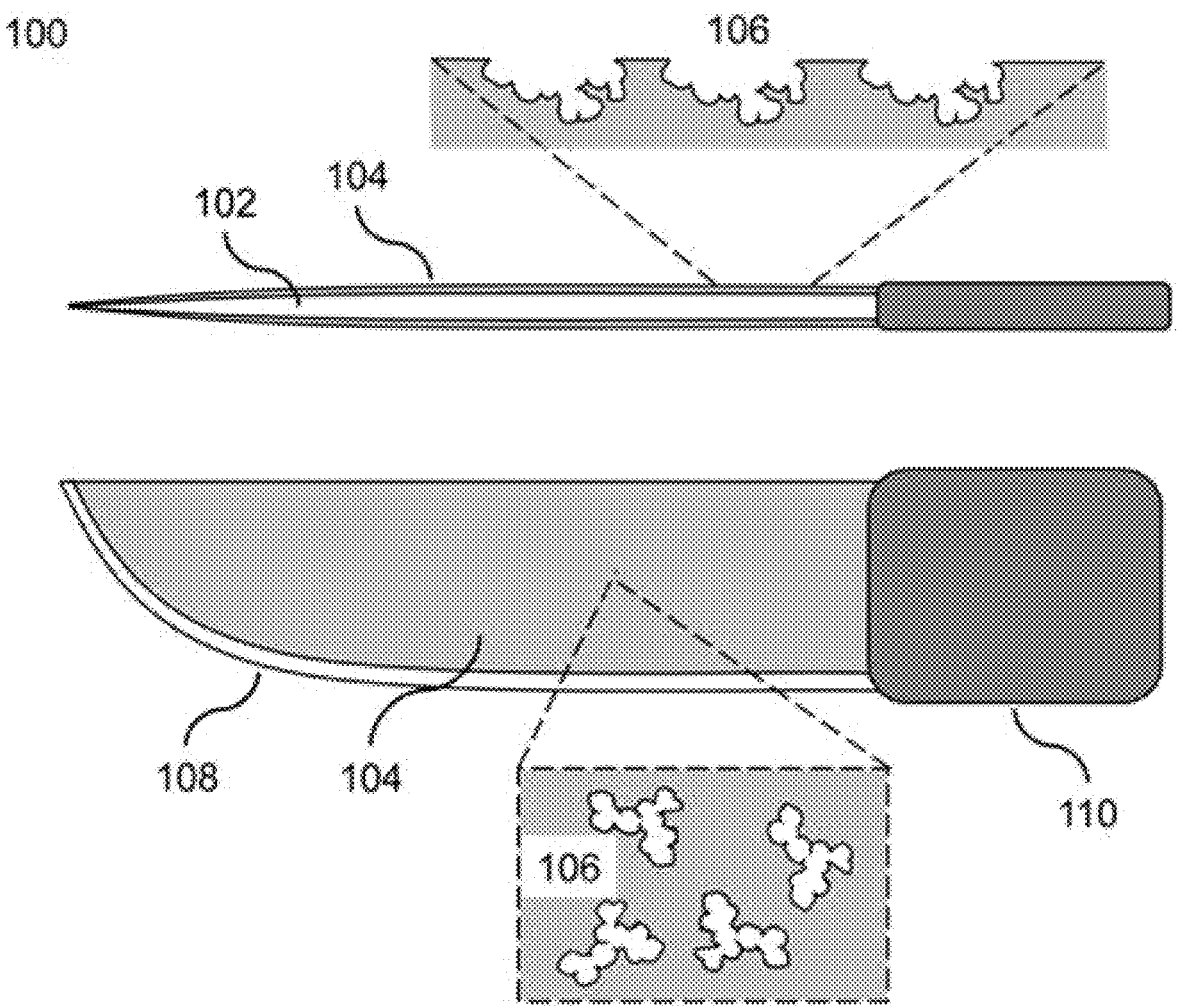
FIG. 1 is a schematic line, surface, and expanded surface drawing depicting a top view and a side view of an embodiment of a molecular imprinted scalpel in accordance with the present invention, showing greatly magnified view of the molecular imprints.

Molecular imprinting is an advancing technique in the medical device field because of its ability to mimic biologically active binding sites. Molecular imprinting uses artificial protein binding sites in order to activate a biological response without the use of heat or foreign blood products. Thus, molecular imprinting has the potential to catalyze blood coagulation. Molecular imprinting may also provide artificial chaperones in potential therapies for protein conformational diseases. Additionally, numerous two-dimensional and three-dimensional techniques are known in the art for imprinting of surface proteins. Techniques using silica have shown successful specificity for imprinting the complex shape of hemoglobin. Biomedical applications have utilized molecular imprinting for ex vivo diagnostic methods such as immunoassays (antibody detection), analytical separations, and biosensors for detecting changes in blood sugar. Molecular imprinting is also used in the development of other biosensors and for diagnostic detection of viruses by interacting with antibodies. Other applications include in vivo therapeutic methods such as the controlled release and delivery of pharmaceutical agents, and the imprinting of fibronectin on synthetic polymer films to produce bioactive scaffolds for tissue engineering.

Current techniques utilize molecular imprinting in biosensors for detecting changes in blood sugar or for interacting with antibodies in ways to provide ex vivo diagnostics. In other instances, techniques such as using silica have shown successful specificity for imprinting the complex shape of hemoglobin. Protein-based molecular imprints have additionally been explored for the detection of virus proteins and even whole viruses, and as artificial chaperones in potential therapies for protein conformational diseases. In most cases, a polymer is cross-linked and co-polymerized in the presence of a target molecule or protein. This target acts as a template for creating a cast. Once the cast is removed, it creates space for an active binding site. Molecular imprinting is supported by extensive research in the last decade, yet the application of imprinting protein-binding sites on scalpel surfaces and other medical devices in order to encourage blood coagulation and other beneficial reactions has not yet been investigated.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided to convey a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagram included herein is generally set forth as a logical flow chart diagram. As such, the depicted order and labeled steps are indicative of one embodiment of the presented reaction. Other steps and reactions may be conceived that are equivalent in function, logic, or effect to one or more steps, or portions thereof, of the illustrated reaction. Additionally, the format and symbols employed are provided to explain the logical steps of the method and are understood not to limit the scope of the reaction. Although various arrow types and line types may be employed in the flow chart diagrams, they are understood not to limit the scope of the corresponding reaction. Indeed, some arrows or other connectors may be used to indicate only the logical flow of the reactions. Additionally, the order in which a particular series of reactions occurs may or may not strictly adhere to the order of the corresponding steps shown.

FIG. 1 depicts an embodiment of a molecular imprinted scalpel 100 in accordance with the present invention. As depicted, the molecular imprinted scalpel 100 comprises a blade 102, a thin polymer film 104, molecular imprints 106 on surface of polymer film 104, a sharp edge for cutting tissue 108 and a blade handle 110. In some embodiments the blade surface 102 is coated with a thin polymer film 104. The molecular imprinted scalpel 100 may comprise without limitation stainless steel, ceramic, plastic, carbon, or other material. The film may be a molecular imprinted polymer 104 with imprinted sites 106 that in various embodiments may initialize, catalyze, and accelerate the wound healing processes such as blood clotting, cell adhesion, and the formation of the extracellular matrix. By mimicking molecules that function as enzymes for these processes, the molecular imprints 106 may promote these beneficial tissue responses directly and immediately as the tissue is cut. Such molecular imprinted polymers have already been demonstrated for proteins that play a major role in blood clotting and wound healing, such as fibrinogen and fibronectin. As the scalpel 100 cuts into the body's tissue, it may, in various embodiments, simultaneously initiate and catalyze blood clotting, wound healing, and other beneficial biochemical processes.

Thus, in some embodiments the molecular imprinted scalpel 100 surface may be tailored to initiate and catalyze a variety of biological processes that could be beneficial to surgery, such as microscopically localized blood clotting, tissue regeneration for wound healing, deadening of cut and proximal nerves to reduce or eliminate the pain of the incision, or inhibition of disease processes such as tumorigenesis, inflammation, or infection. Bleeding may thus be stemmed without the use of heat and its consequential damage to tissue, and the scalpel can act on the tissue in other beneficial ways that are not possible with current technology. The surface of the molecular imprinted scalpel 100, could also be tailored to genetically dependent pathologies or health conditions of patients. Such "personalized" molecular imprinted scalpels 100 might be particularly useful for patients with bleeding disorders such as hemophilia, or to cancer patients wherein the malignant cells respond to chemical manipulation of specific cell receptors.

In certain embodiments the molecular imprinted scalpel 100 mitigates bleeding during surgery. As the molecular imprinted scalpel 100 cuts into the body's tissue, it may simultaneously initiate and catalyze blood clotting. With the use of specific molecular imprinted catalytic sites, the relevant biochemical pathways of the blood coagulation cascade may be "kick-started" and accelerated to arrest bleeding from cut blood vessels. In various embodiments areas of use include, for non-limiting example, surgery where bleeding, heat, and tissue damage cannot be tolerated such as in the central nervous system, joints, and lungs. The molecular imprinted scalpel 100 could have an advantage over a scalpel that would stop bleeding by injecting blood-coagulating chemicals. With the molecular imprinted scalpel 100, the blood clotting may be localized to a microscopic region at the cut ends of the blood vessels, and thus unlikely to form large blood clots that could be dangerous in the brain or lung.

Certain embodiments of the molecular imprinted scalpel 100 provided herein are configured to catalyze and promote wound healing mechanisms at the cut surface of the tissue. For example, a principal mechanism for wound healing involves the glycoprotein fibronectin, which binds to integrins and extracellular matrix proteins such as collagen and fibrin. Fragmentation of fibronectin is also a key wound healing mechanism, which induces wound contraction. The adsorption of fibronectin onto polymer surfaces has been reported in the literature, and the ability to imprint fibronectin molecules, similar glycoproteins, and proteases which fragment fibronectin onto a polymer surface would allow the use of these imprints as catalytic sites for wound healing.

The molecular imprinted scalpel 100 may comprise molecular imprints 106 of analgesic molecules to inhibit pain receptors on cut nerve endings as they are sliced through by the scalpel 100, rendering surgical incisions less painful to the patient or possibly even painless. Imprints of molecules catalyzing homeostasis may enable patients to heal faster with less pain. These features may lead to reduction in surgical painkillers or local anesthesia. Disrupting PSD85-nNOS protein-protein interactions may be effective in attenuating pathological pain without producing motor axazia of the N-methyl-D-aspartate receptor NMDAR antagonists. This capability may eventually mitigate the need for anesthesia. Molecular imprinted scalpels may also disrupt the PSD85-nNOS protein-protein interactions that cause long-term pain.

In some embodiments the molecular imprinted scalpel 100 provides a therapeutic potential. Molecular imprints 106 on the blade 102 may act as chemotherapy agents on the tissue surface at the incision site to prevent recurrence of cancer or diminish other disease processes such as inflammation. Such an embodiment may be useful in cancer surgery of soft tissue, such as breast cancer, where obtaining a negative (clean or cancer-free) surgical margin is important for reducing recurrence of the disease. Moreover, tumorigenesis is often accompanied by angiogenesis. Once a tumor has been surgically excised, remaining cancer cells at the incision site (the margins) have the potential to regrow. Many tumor cells secrete angiogenic factors, notably VEGF. In particular, metastatic tumor cells overexpress the VEGF gene, which allows them to grow and metastasize. An angiogenesis inhibitor imprinted on the scalpel blade 102, such as a VEGF inhibitor, could therefore be valuable for preventing recurrence of many types of cancers.

In various embodiments the molecular imprinted scalpel 100 may modify the biomechanical properties of the tissue surface at the incision site. Tumorigenesis and tumor progression are usually preceded by malignant cells releasing metalloproteinases and other enzymes that soften the extracellular matrix, allowing the tumor to infiltrate normal tissue and to spread. The molecular imprinted scalpel 100 may comprise imprints 106 of molecules that could inhibit either the secretion or action of the metalloproteinases and other enzymes. The tissue surface could thus be "inoculated" at the incision site against the regrowth of the excised cancer.

A molecular imprinted polymer 104 may be created by mixing monomers of the polymer with the molecule (known as the template) to be imprinted. First, the monomers cluster and conform around the template. Second, the monomers polymerize with the template in place. Third, the template is removed from the polymer, thus leaving a mold or imprint of the molecule in a polymer matrix. The monomers can be polymerized into nanoparticles or thin films. To create the molecular imprinted scalpel 100 described herein, the monomers may be polymerized as a thin film 104 on the blade 102 of a scalpel.

Various methods for the fabrication of molecular imprinted polymers as thin films on a solid substrate are known in the art, and include spin coating, polymer brushes, dip coating using a silicon substrate, self-assembling monolayers, drop coating, spray coating, grafting, electropolymerization, and sol-gel processes. Micropatterned thin films of molecular imprinted polymers can also be manufactured using various lithography methods such as UV-mask lithography, soft lithography, microstereo-lithography, and nanoimprint lithography.

The molecular imprinted scalpel 100 may be fabricated in a variety of different models consisting of different sets of molecular imprints 106. A model could then be available for each particular type of surgery (for example, neurosurgery) or disease (for example, metastatic breast cancer). Many diseases are genetic in origin and nature, and may thus be cured or mitigated with treatments tailored or "personalized" to the patient. Therefore, in some embodiments the molecular imprinted scalpel 100 incorporates personalized treatment options. Molecular subtypes are a relatively new method for classifying cancer with gene or protein sequencing methods. Most importantly, the molecular subtypes have been found to provide more accurate diagnostic and prognostic information than conventional histopathology, and are now being used to guide oncologists in the personalized treatment of breast cancer. One example of the personalized application of the molecular imprinted scalpel 100 is to the HER2+ subtype of breast cancer. With HER2+ breast cancer, the cancer cells exhibit overexpression of HER2 receptors on the cell membrane. HER receptors are a family of proteins that play a major role in multiple signaling pathways in the cell, and their overexpression leads to unrestrained cell proliferation and tumorigenesis. HER2-inhibitors are therefore being developed and clinically used to target the HER2 receptor and stop the cell proliferation mechanism. Embodiments of the molecular imprinted scalpel 100 with imprints 106 that mimic the action of HER2-inhibitors could interact with HER2+ breast cancer cells during surgery, and thus inhibit the regrowth of malignant tissue along surgical margins.

In some embodiments an electronically generated physical mechanism may prevent proteins from becoming trapped on the surface of the scalpel blade 104. Ultrasonic waves may be generated in the handle 110 of the scalpel 100 and transmitted to the scalpel blade 104 via waveguide principles, such as by an acoustic waveguide (the metal of the blade). Such waveguide principles are identical to those used to propagate light along an optical fiber.

In certain embodiments imprinted molecules for stopping bleeding further comprise the Von Willebrand factor, which make platelets more sticky. Vasoconstriction may be encouraged administration of Ca2+. Various embodiments comprise imprints of vasoconstrictors. These may include, without limitation, ephedrine—a crystalline alkaloid drug obtained from ephedras and typically used to relieve asthma and hay fever—that causes vasoconstriction and widening of the bronchial passages by increasing activity of norepinephrine on adrenergic receptors; antihistamines; endothelin—the most powerful known vasoconstrictor—which is secreted from endothelial cells when a blood vessel is cut; cocaine, which as anesthetic effects and stimulates the release of endothelin; Phenylephrine; and caffeine.

In some embodiments imprinted molecules comprise thromboxane A2 to foster arterial constriction and platelet aggregation. Clotting factor 9a, which leads to many thousands of times of production of 10 and 10a, is sometimes imprinted. Catalysts such as factor 8, 8a, 5, and 51 may be imprinted separately or in combination. In various embodiments PAR-1 and PAR-4 are imprinted to activate thrombin. Various signaling molecules may be imprinted to induce vasoconstriction including without limitation alpha adrenoreceptors (agonists) such as A1 which is linked to gq proteins that activate smooth muscle contraction through 1P3 receptors and A2 which is linked to gi proteins and binding of alpha agonist which decreases intracellular cAMP. In some embodiments vasoconstrictors, catalysts, signaling molecules and other molecules are administered directly in combination with the use of the molecular scalpel 100.

Figure 2:
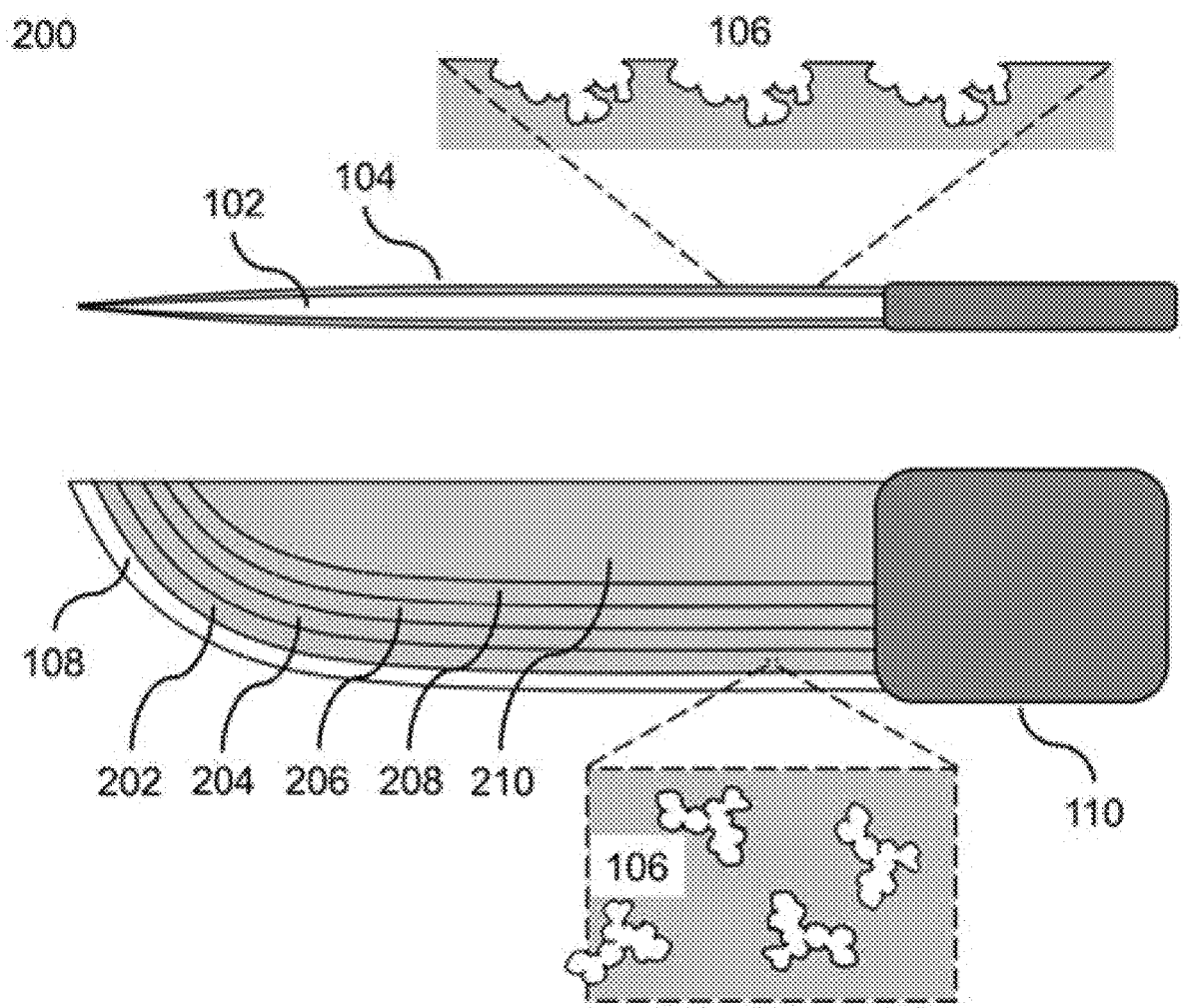
FIG. 2 is a schematic line, surface, and expanded surface drawing depicting a top view and a side view of an embodiment of a multi-layer molecular imprinted scalpel in accordance with the present invention, showing a greatly magnified view of the molecular imprints.

FIG. 2 depicts an embodiment of a multi-layer molecular imprinted scalpel 200 in accordance with the present invention. As depicted, the multi-layer molecular scalpel 200 comprises a blade 102, a thin polymer film 104, molecular imprints 106 on surface of polymer film 104, regions 202, 204, 206, 208, 210 of molecular imprints 106, and a sharp edge for cutting tissue 108. The patterned molecular imprinted scalpel 200 may comprise without limitation stainless steel, ceramic, plastic, carbon, or other material. Vasoconstrictors may be positioned closest to the cutting edge 108 or the blade 102. PAR-1 imprints and PAR-4 imprints and other imprints may be sequenced in regions of molecular imprints 106 further from the cutting edge 108.

Ephedrine has been used in molecular imprinting through the following titration method: Ephedrine and distilled 2-hydroxyethylmethacrylate (HEMA) are dissolved in a dry solvent with a polymer and cross-linker and transferred to a container for polymerization by UV radiation. The polymerized sample is ground by mortar and pestle and rinsed with acetone. Afterwards, the imprint is gradually extracted with methanol.

The next strategically placed imprints 106 as shown on the molecular imprinted blade 102 may be those of PAR-1 and PAR-4. Imprinting of PAR-1 and PAR-4 may be accomplished through template imprinting techniques. PAR-1 and PAR-4 are obtained as a template by absorption onto a silicate mineral along with a buffer. The sample is heated and left to cool. Afterwards the sample is rinsed with deionized water to remove the buffer. The remaining sample may be coated with a disaccharide. A plasma deposition (hexafluoropropylene) may be deposited onto the sample where it will be placed in a plasma reactor to remove the protein. Finally, a solvent may wash away any remains of the protein.

In certain embodiments the thin polymer film 104 covers majority of blade 102 area for biochemically interacting with the tissue. Each region 202, 204, 206, 208, 210 sometimes contains molecular imprints 106 specific for initiating and catalyzing each successive step in a complex biochemical process such as blood clotting, anesthetizing nerve endings, and/or other processes.

In various embodiments a pattern of molecular imprints 106 of different molecular species on a polymer film 104 may be used to induce a time sequence of biomolecular interactions to reproduce complex, time-evolving biological processes in tissue. The imprint species sometimes varies according to region 202, 204, 204, 208. As the multi-layer molecular imprint scalpel 200 cuts through tissue, the different regions 202, 204, 206, 208 may come into contact with the cut tissue sequentially in time, and therefore may initiate different stages in a time-evolving biological process such as the blood coagulation cascade.

In summary, molecular imprints function as "phantom" or "virtual" molecules to enhance blood clotting or other reactions directly at the incision by activating and promoting natural biochemical responses such as, for non-limiting example, the blood coagulation cascade, the elimination of damaged (cut) cells, and healing processes. These processes are localized to a microscopic region touching the surface of the surgical blade, and therefore do not affect surrounding tissue as do energy-based scalpels. This same biofunctional surface may be applied to the surface of other medical devices including those described below to minimize bleeding and scarring, to hasten healing, and/or provide other benefits.

Figure 3:
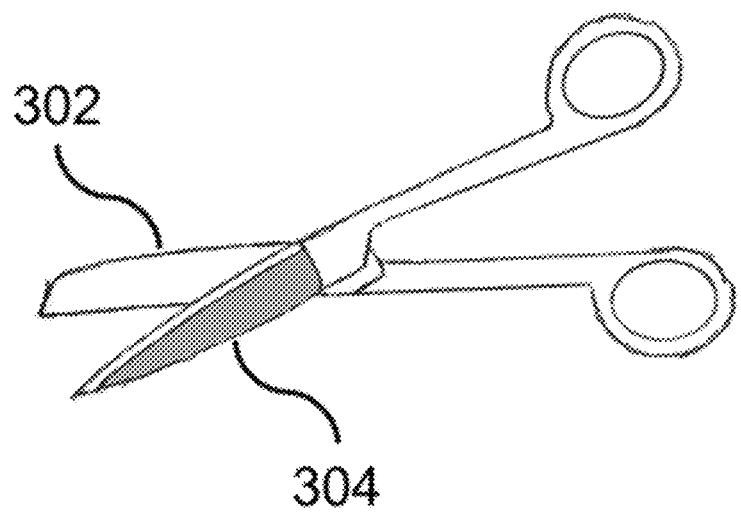
FIG. 3 is a schematic line and surface drawing depicting an embodiment of a molecular imprinted surgical scissor in accordance with the present invention.

FIG. 3 depicts an embodiment of a molecular imprinted surgical scissor 300 in accordance with the present invention. As depicted the surgical scissor 300 comprises a blade 302 and a molecular imprinted thin polymer film 304. In certain embodiments the molecular imprinted polymer film 304 is deposited on the non-cutting surface of the blade 302 and thus may contact the tissues immediately adjacent to the cut without interfering with the function of the scissor 300. In some embodiments the surgical scissor 300 comprises stainless steel. The surgical scissor 300 sometimes comprises without limitation ceramic, plastic, carbon, or other material. In various embodiments the technology provided herein uses molecular imprinting on a surgical or medical device such as the molecular imprinted surgical scissor 300 to create enzymatic sites in order to initiate biomolecular processes of the adjacent tissue and to accelerate their reaction rates. In addition to this enhancement of the biomolecular reactions by the imprints, additional means could be used to increase the enzymatic activity of the molecular imprints.

Figure 4:
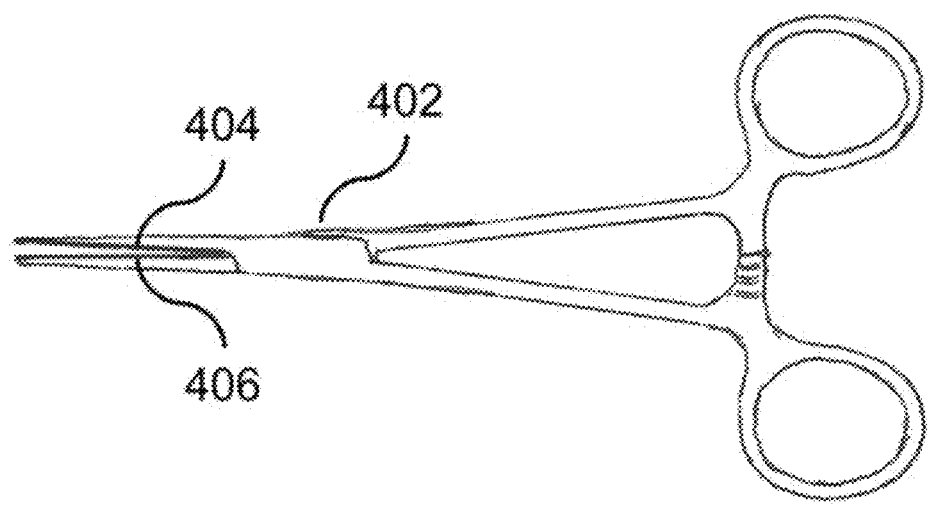
FIG. 4 is a schematic line drawing depicting an embodiment of a molecular imprinted forceps or clamp in accordance with the present invention.

FIG. 4 depicts an embodiment of a molecular imprinted forceps or clamp 400 in accordance with the present invention. As depicted the molecular imprinted forceps or clamp 400 comprises a body 402, a blade 404, and a molecular imprinted polymer film 406 on the tissue-grasping surface of each blade 404. The molecular imprinted forceps 400 may comprise without limitation stainless steel, ceramic, plastic, carbon, or other material. The molecular imprinted polymer film 406 may comprise for non-limiting example molecule imprints to promote blood clotting, healing, and/or pain relief as well as to discourage infection, inflammation, and tissue necrosis.

Figure 5:
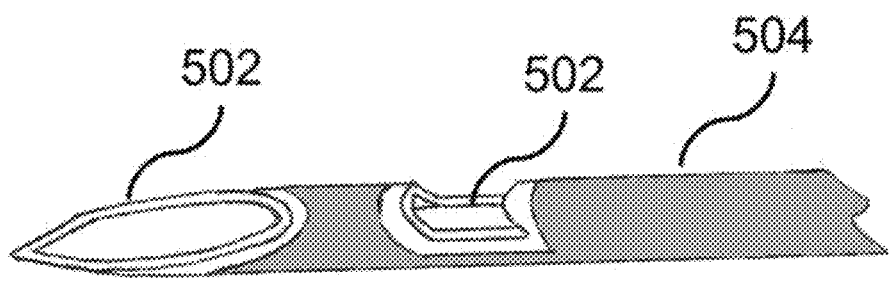
FIG. 5 is a schematic line and surface drawing depicting a magnified view of an embodiment of the tip of a molecular imprinted biopsy, hypodermic, or intravenous needle in accordance with the present invention.

FIG. 5 depicts a magnified view of an embodiment of the tip of a molecular imprinted biopsy, hypodermic, or intravenous needle 500 in accordance with the present invention. As depicted the molecular imprinted needle 500 comprises a hollow body 502 and a molecular imprinted polymer film 502 on the outer surface of the hollow body 502. The molecular imprinted needle 400 may comprise without limitation stainless steel, ceramic, plastic, and carbon. The molecular imprinted polymer film 502 may comprise for non-limiting example molecule imprints to promote blood clotting, healing, and/or pain relief as well as to discourage infection, inflammation, and tissue necrosis.

Figure 6:
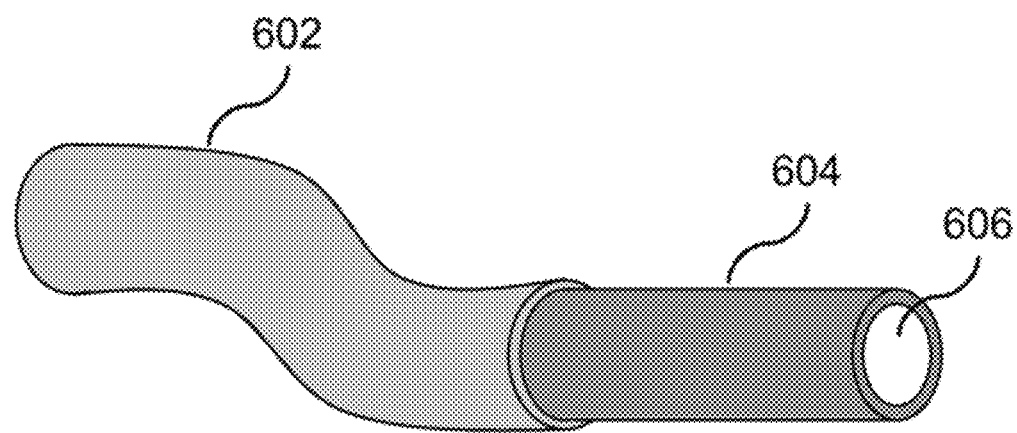
FIG. 6 is a schematic line and surface drawing depicting a cutaway view of an embodiment of a molecular imprinted catheter in accordance with the present invention.

FIG. 6 depicts a cut-away view of an embodiment of a molecular imprinted catheter 600 in accordance with the present invention. As depicted the molecular imprinted catheter 600 comprises a body 604, a hollow interior 606, and a molecular imprinted polymer film 602. The molecular imprinted catheter 600 may comprise rubber, plastic, carbon fiber, fabric, metal or other material. The molecular imprinted polymer film 602 may comprise for non-limiting example molecule imprints to promote blood clotting, healing, and/or pain relief as well as to discourage infection, inflammation, irritation, and tissue necrosis.

Figure 7:
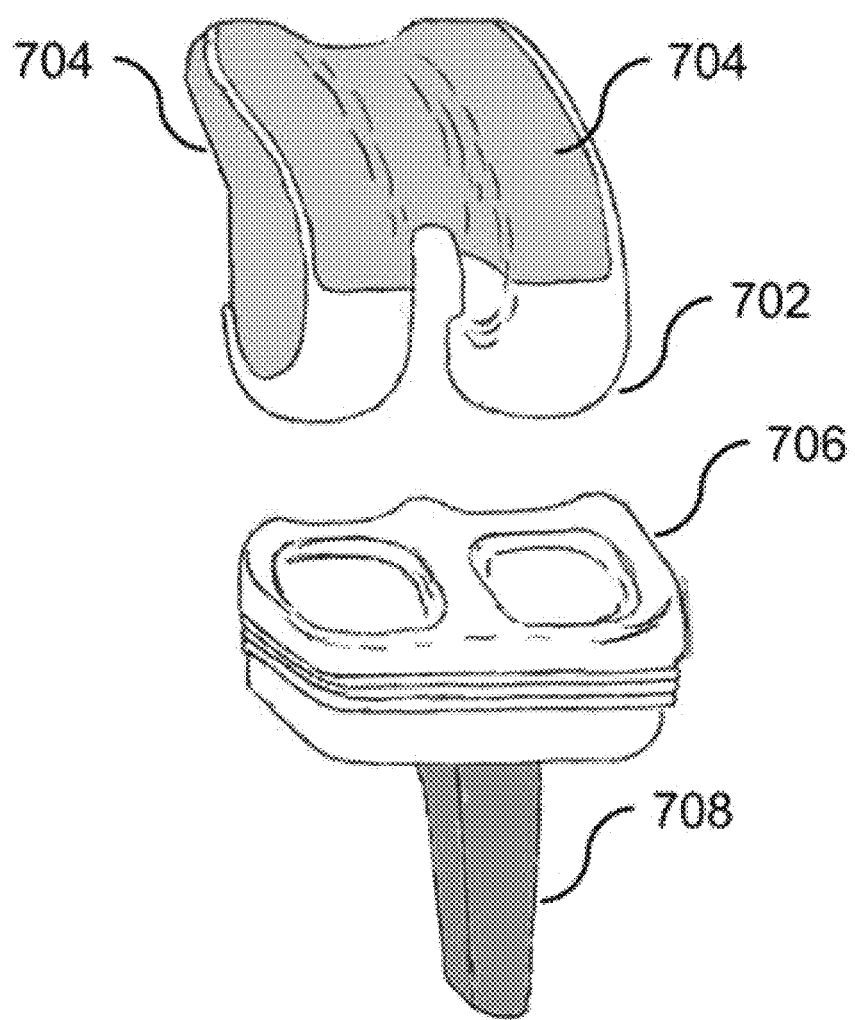
FIG. 7 is a schematic line drawing and surface depicting an embodiment of a molecular imprinted artificial joint (here a knee) in accordance with the present invention.

FIG. 7 depicts an embodiment of a molecular imprinted artificial joint 700 (here a knee) in accordance with the present invention. As depicted the artificial joint 700 comprises an upper joint body 702, a molecular imprinted polymer film 704, a lower joint body 706 and a stem 708. In certain embodiments the molecular imprinted polymer film 704 is applied to the joint 700 surfaces that contact tissue but not to the moving surfaces that contact other joint 700 surfaces. The molecular imprinted artificial joint 700 may comprise titanium, stainless steel, polyethylene, cobalt chromium alloys, ceramic, plastic, carbon, tantalum, zirconium alloy, oxinium alloy or other material. The molecular imprinted polymer film 704 may comprise for non-limiting example molecule imprints to promote blood clotting, healing, bone regeneration, vascularization, and/or pain relief as well as to discourage infection, rejection, inflammation, and tissue necrosis.

In certain embodiments the molecular imprints comprise different types of molecules. One set of molecules could produce an antimicrobial effect, another could mimic an anticoagulant, and another could function as an immunosuppressant. The action may be localized to the implant surface to avoid adverse effects to the surrounding tissue. Multiple types of imprints are used in certain embodiments of other devices provided herein. In such cases the proportion of molecular actions might be tailored or custom designed for devices of specific function (e.g., artificial joints versus DBS electrodes), for specific regions in the body (e.g., urinary versus venous catheters), or for patients with specific conditions (hemophilia, poor healing due to diabetes, immunosuppressed, etc.).

Figure 8:
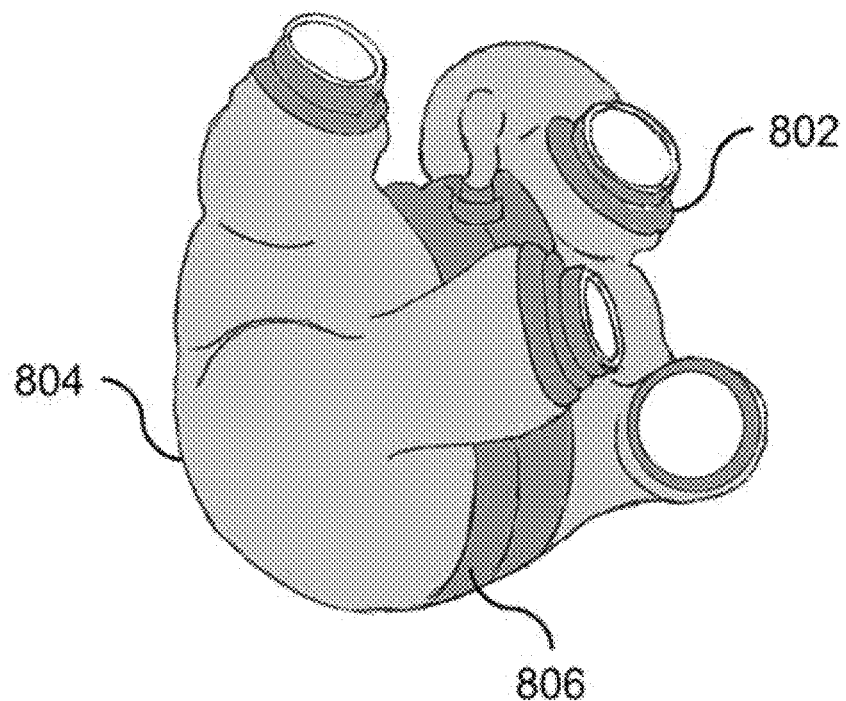
FIG. 8 is a schematic line and surface drawing depicting an embodiment of a molecular imprinted artificial organ (here a heart) in accordance with the present invention.

FIG. 8 depicts an embodiment of a molecular imprinted artificial organ 800 (here a heart) in accordance with the present invention. As depicted, the artificial organ 800 comprises a body 806, connection points 802, and a molecular imprinted polymer film 804. The molecular imprinted artificial organ 800 may comprise any appropriate material as known in the art. The molecular imprinted polymer film 804 may comprise for non-limiting example molecule imprints to healing, tissue regeneration, vascularization, and/or pain relief as well as to discourage infection, rejection, inflammation, and tissue necrosis and promote or prevent blood clotting.

Figure 9:
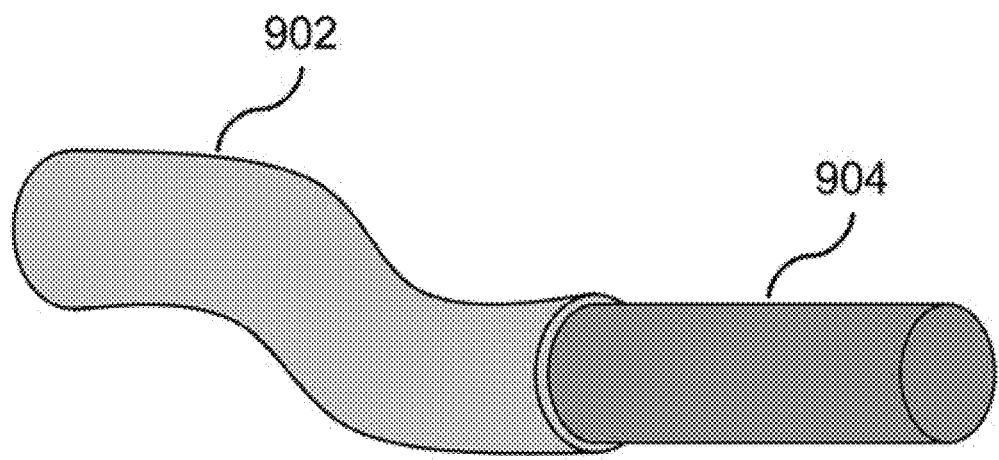
FIG. 9 is a schematic line and surface drawing depicting a cutaway view of an embodiment of an electrode coated with a molecular imprinted polymer in accordance with the present invention.

FIG. 9 depicts a cutaway view of an embodiment of an electrode 900 coated with a molecular imprinted polymer in accordance with the present invention. As depicted the electrode 900 has a body 902 and a molecular imprinted polymer coating 904.

Figure 10:
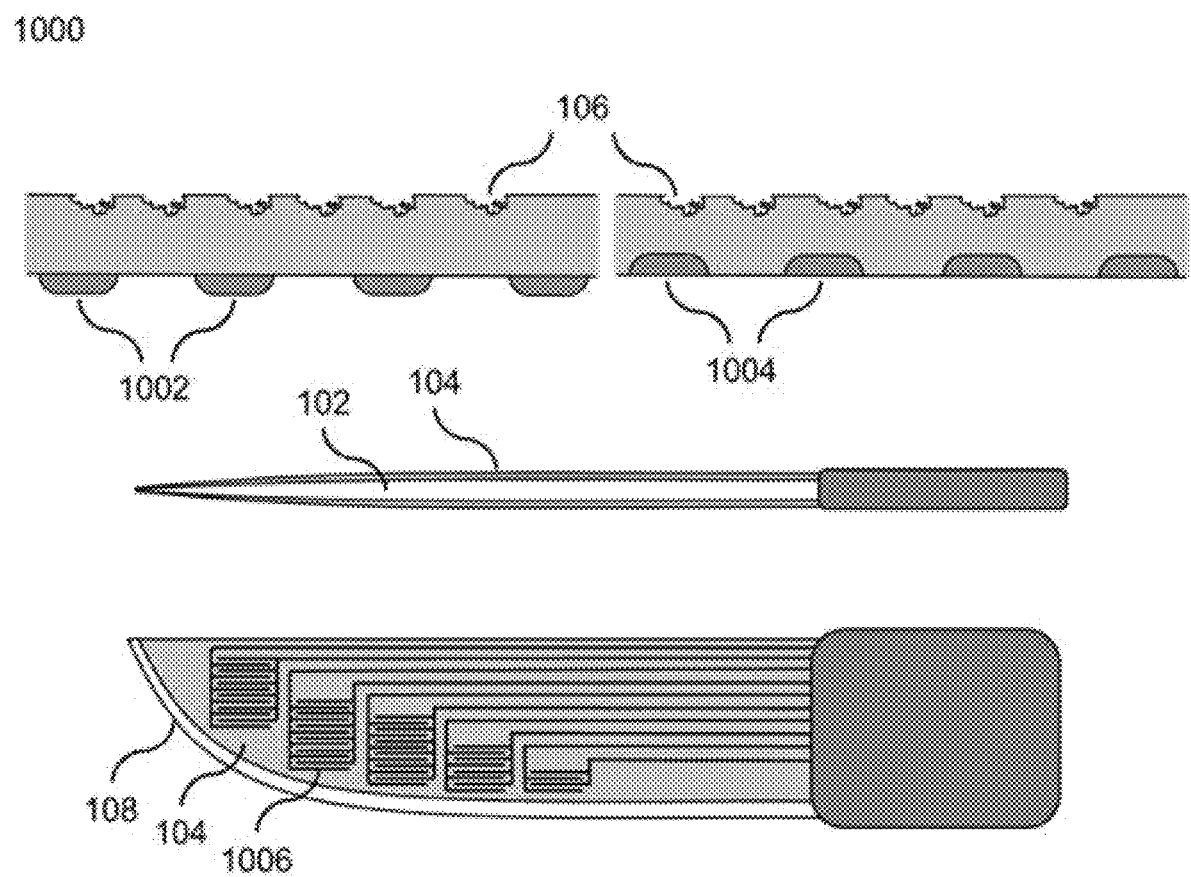
FIG. 10 is schematic line, surface, and expanded surface drawing depicting a section view of an embodiment of an electronically enhanced molecular imprinted scalpel in accordance with the present invention, showing interdigital electrodes embedded within a scalpel blade and positioned on the surface of the blade and biosensors in accordance with the present invention.

FIG. 10 depicts an embodiment of an electronically enhanced molecular imprinted scalpel 1000 in accordance with the present invention. As depicted the electronically enhanced molecular imprinted scalpel 1000 comprises a blade 102, a polymer coating 104, molecular imprints 106, a sharp cutting edge 108, and interdigital electrodes 1006 embedded within a scalpel blade 1004 and/or positioned on the surface of the blade as biosensors 1002. Molecular imprinted polymers have capability as biosensors for biomolecules as well as enzymes for biomolecular processes. In certain embodiments the electronically enhanced molecular imprinted scalpel 1000 detects tissue pathologies as it cuts through the tissue. In certain embodiments the electronically enhanced molecular imprinted scalpel 1000 detects biomarkers from breast cancer cells during breast conservation surgery (lumpectomy), thereby alerting the surgeon in real time on whether the surgical margins are negative (cancer-free) or positive for cancer cells. Various embodiments may be used for many types of cancer surgery in soft tissue, including brain and lung cancer. Similarly, the presence of cytokines could alert the surgeon to the presence of inflammation or infection.

Biosensing molecular imprinted polymer surface technologies include surface plasmon resonance (SPR) techniques, surface-enhanced Raman spectroscopy (SERS), fluorescence quenching of semiconductor quantum dots, photoluminescence, UV-visible spectroscopy, electrochemical sensors (conductivity, capacitance, impedance, potentiometry, and voltametry measurements), piezoelectric (quartz crystal microbalance) sensors, and biomimetic microchips with micropatterned imprinted polymers. The molecular imprint biofunctional devices provided herein may combine biosensors with bioactive molecular imprints, and apply them to surgical devices such as a scalpel for in vivo sensing of tissue state and pathology.

Figure 11:
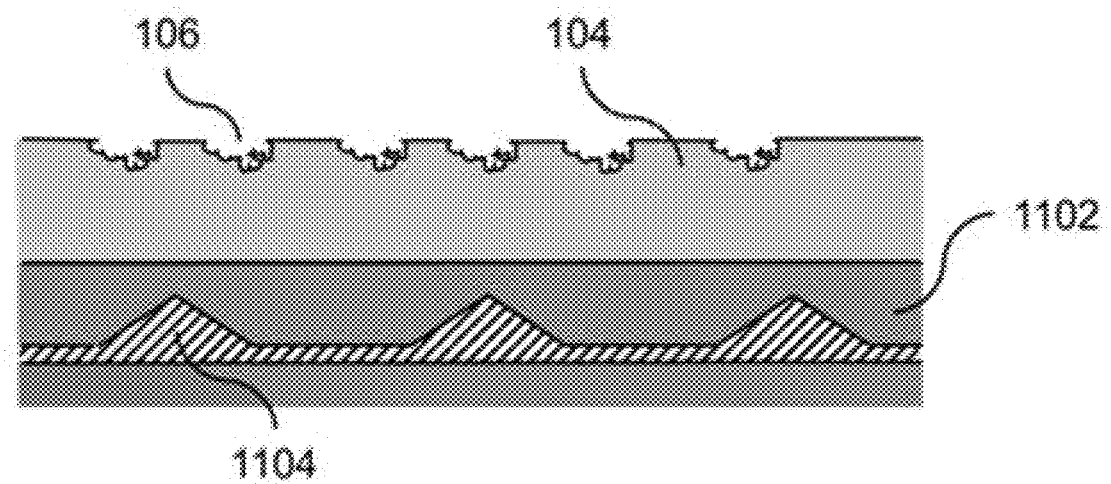
FIG. 11 is a schematic line and surface drawing depicting an expanded section view of an embodiment of an electronically embedded molecular imprint scalpel in accordance with the present invention, showing semiconductor and nanoparticle quantum dots embedded within a scalpel blade in accordance with the present invention.
Figure 11:
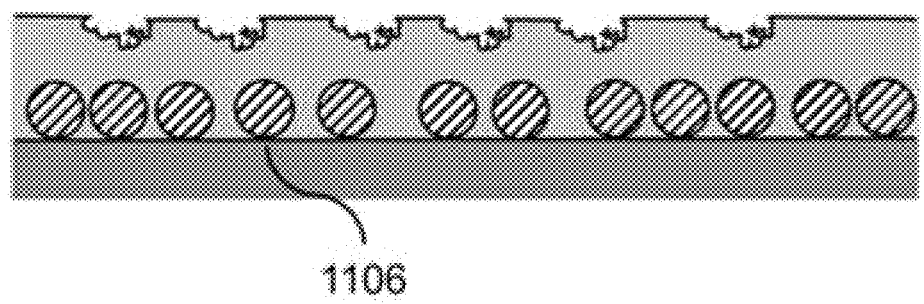

FIG. 11 depicts an expanded section view of an embodiment of an electronically embedded molecular scalpel 1100 in accordance with the present invention. As depicted the electronically embedded molecular imprinted scalpel 1100 comprises a blade 102, a polymer film 104, molecular imprints 106, an embedded semiconductor 1102, and embedded quantum wires or nano-islands or nanoparticle quantum dots 1106. In some embodiments quantum dots underneath the molecular imprints are used to increase enzymatic reaction rate. In certain embodiments the quantum dots, nano-islands, or wires are custom-engineered to produce unique electron wave function configurations that modulate the response of the molecular imprints. The quantum dots, nano-islands, or wires may therefore be used to dynamically reconfigure the electron charge distribution within the molecular imprints, thereby creating a tunable molecular imprint at the quantum level. Such charge distribution may influence biochemical process such as blood clotting or anesthetizing nerve endings.

For non-limiting example, static electric fields (also known as direct-current or DC fields) have been shown to enhance the catalytic rate of the enzyme ketosteroid isomerase, and may have similar effects on a broad range of biomolecular interactions. Static electric fields have also been shown to have significant effects on the biomechanical properties of cells, indicating that they influence the cytoskeletal network and proteins. Such static electric fields are sometimes generated on the surface of the electronically enhanced molecular imprinted scalpel 1000, the electronically embedded molecular imprinted scalpel 1100 or joint replacement 700 with the use of interdigital electrodes deposited onto or into the surface of an insulating material (e.g., diamond or diamond coated), but lying beneath the polymer film 104 and corresponding molecular imprints 106.

In various embodiments electric fields, ultrasonic waves, light, or quantum dots provide additional energy to free molecules from the imprint binding sites. This may be useful not only in the fabrication of the molecular imprints, but also in re-activating the enzymatic function of imprint sites that have been de-activated by the bonding of free molecules to the imprints.

In certain embodiments high frequency ultrasonic waves (10 MHz-10 GHz) or light (infrared to ultraviolet) increase the enzymatic reaction rates of the molecular imprints 106. The ultrasonic or light waves may be generated in the handle 110 of the electronically enhanced molecular imprinted scalpel 1000 or the electronically embedded scalpel 1100 and transmitted to the scalpel blade 102 via waveguide principles, such as by an acoustic waveguide (the metal of the blade) or an optical fiber embedded into the blade. Alternatively, the blade 102 may comprise a semiconductor such as silicon into which ultrasonic transducers or lasers could be fabricated on microchips and embedded into the blade 102 to locally excite the molecular imprints.

In certain embodiments high-frequency ultrasonic waves (10 MHz-10 GHz) are generated locally in the blade 102 of the scalpel using embedded piezoelectric elements and conductive electrodes (i.e., an electronically embedded scalpel). In some embodiments an ultrasonic surface wave is generated on the molecular imprinted blade that mechanically agitates bound protein molecules and induces their separation from the imprints.

Figure 12:
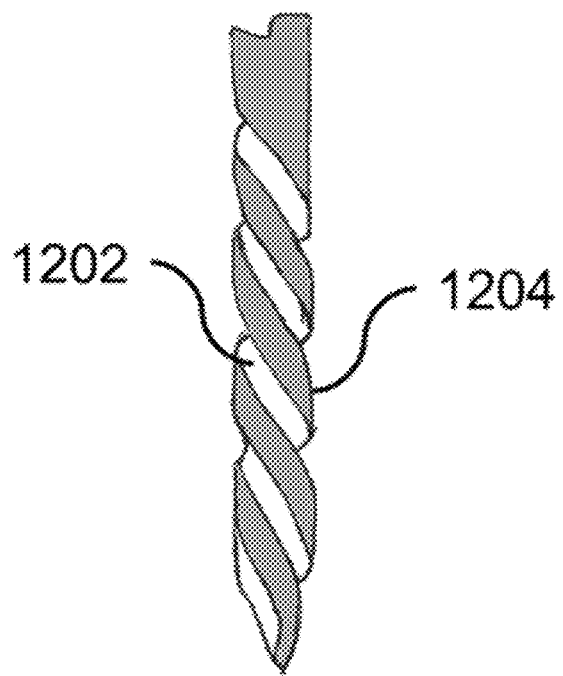
FIG. 12 is a schematic line and surface drawing depicting an embodiment of a molecular imprinted cutting tool (here a drill bit) in accordance with the present invention.

FIG. 12 depicts an embodiment of a molecular imprinted cutting tool 1200 (here a drill bit) in accordance with the present invention. As depicted, the molecular imprinted cutting tool 1200 comprises a cutting surface 1202 and a molecular imprinted polymer film 1204. Thus, the embodiments of this invention could also be extended beyond the field of medicine. For example, molecular imprinted knives could be used to reduce the threat of food contamination by both inhibiting the transfer of pathogens on knife surfaces, and by sensing the presence of pathogen biomarkers. In manufacturing, molecular imprinted cutting tools could be used to instantly treat the surfaces of soft polymers and other suitable materials during the cutting process. Such surface treatments include enhancing the cross-link density of a polymer on its cut surface to protect the material, or changing the polarity of the cut surface to render the surface hydrophobic or hydrophilic.

Figure 13:
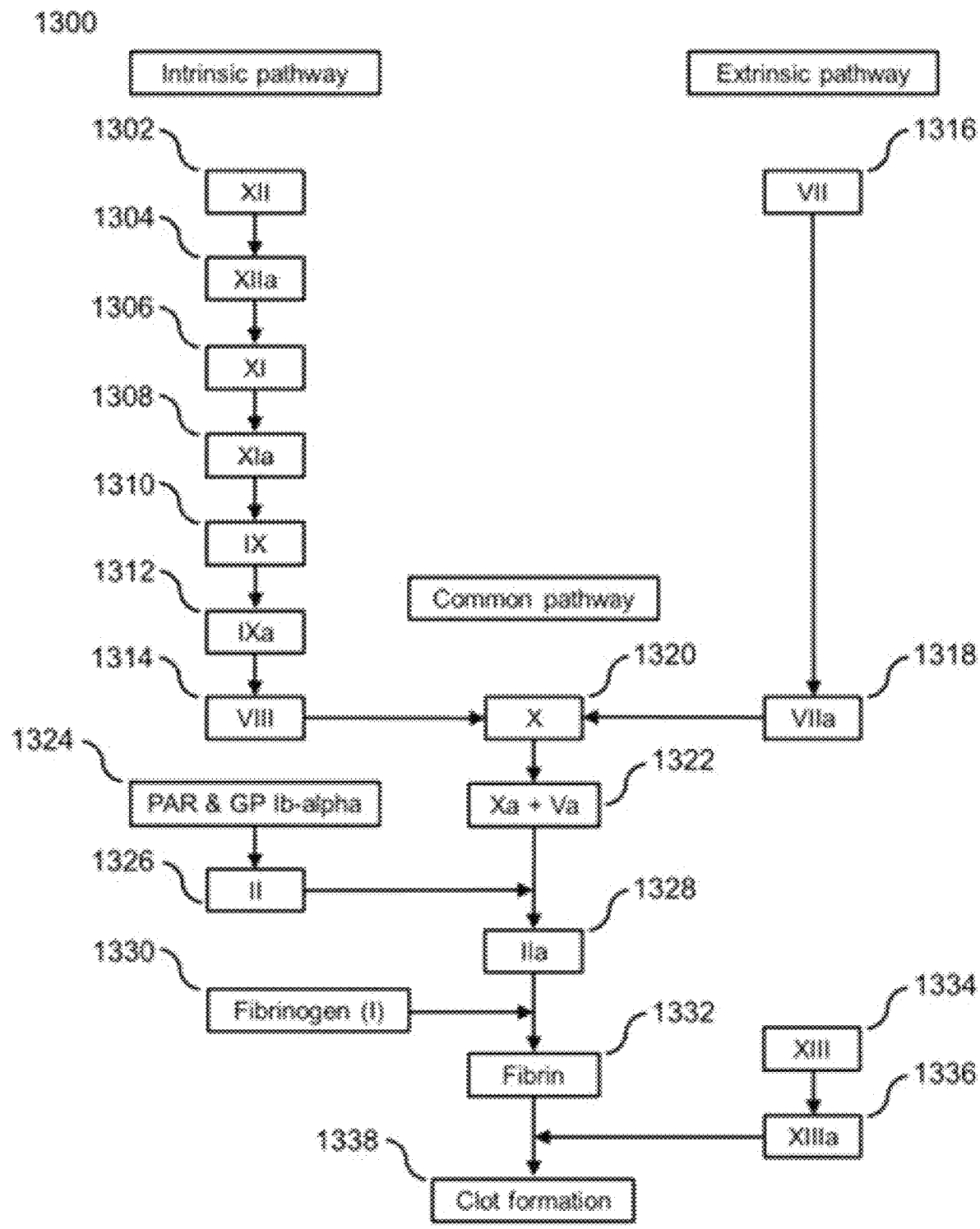
FIG. 13 is a schematic flow chart diagram depicting intrinsic and extrinsic blood clotting pathways.

FIG. 13 depicts the blood coagulation pathway 1300 following the initiation of the extrinsic and intrinsic pathways by way of damage to a blood vessel. In the extrinsic pathway, factor VII 1316 activates factor VIIa 1318 until there is enough initial thrombin for this pathway to become inhibited (inhibitor not shown). From there the common pathway is activated with the help of the enzyme Factor V. Simultaneously, in the intrinsic pathway, factor XII 1302 activates factor XIIa 1304, followed by factor XI 1306 and Xia 1308. At this point in the pathway, (not shown) factor VIIa from the intrinsic pathway helps to activate factor IX 1310 and thus factor Ixa 1312. From there, the enzyme factor VIII 1314 catalyzes the common pathway. The use of this catalyzation from both factor VIII and factor V allows for activation of factor X 1320 to Xa 1320 many thousand times. This begins the common pathway where factor II (prothrombin) 1326 activates factor IIa (thrombin) 1328, leading to the conversion of fibrinogen 1330 to fibrin 1332.

The names of these two pathways are given to mean that the extrinsic pathway is activated by factors released directly by endothelial cells in the vessel wall and the intrinsic pathway is the extrinsic-activated pathway that is carried out though activation by blood platelets. In a sense, the extrinsic pathway or factors that are released at the site of the damaged vessel wall can initially activate platelets, but because of the manner in which platelets function independently in activating a series of different factors, they are seen as having their own pathway. Ultimately both pathways lead to the same event or "common pathway" that activates thrombin, the converter of fibrinogen to fibrin.

Blood clotting mechanisms involve PAR and GP Ib-alpha on thrombin. The natural process of hemostasis occurs though multistep activation of several tissue factors through two main pathways known as intrinsic and extrinsic pathways.

When tissue is cut, endothelial cells present in the walls of blood vessels release vasoconstrictors, namely thromboxane A2 and Von Willebrand factor. Once activated, platelets aggregate to the site of the damaged vessel to form a platelet plug. This plug is later reinforced by blood coagulation. Additionally, exposed endothelial tissue and collagen cause activation of platelets that in turn activate and emit thromboplastin and lipoprotein, which aid in the intrinsic pathway. Thromboplastin activates a series of clotting factors. Enzymatic activation of these clotting factors eventually leads to activation of thrombin, which converts fibrinogen to fibrin. As blood coagulation is occurring, further reinforcement of the platelet plug gradually reduces until cell growth and clotting reach equilibrium where fibrin is slowly dissolved by plasmin, leading to an intact vessel wall.

Thrombin is known to contribute to clotting by causing the shape change of platelets. In vitro, when thrombin is added to human platelets, the platelets not only change their shape, they stick to each other and secrete the contents of their storage granules. Protease-activated receptors (hereinafter PAR) such as PAR-1 and PAR-4 receptors have been shown to be key components of thrombin activation. If imprinted, PAR-1 is shown to be key in activation of low thrombin concentration while PAR-4 is shown to activate with high threshold of thrombin. Use a molecularly imprinted PAR-1 and PAR-4 in strategic locations located on the scalpel blade 102 could increase thrombin activation by catalyzing fibrinogen conversion to fibrin thus speeding up blood coagulation. Additionally, the binding of thrombin to GP Ib-alpha could facilitate cleavage of PAR-4 to platelets, which could also help speed up clotting at the site of an incision.

Figure 14:
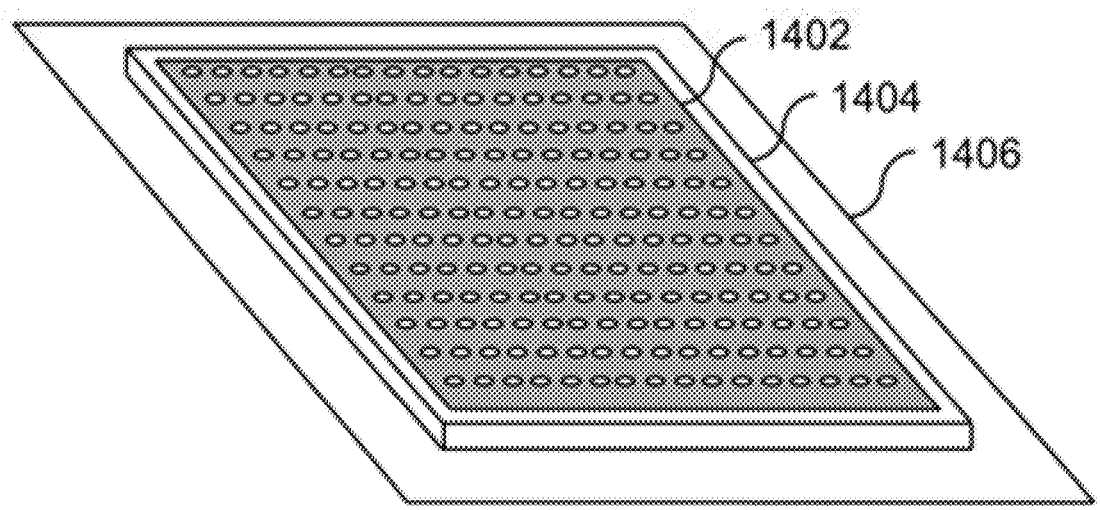
FIG. 14 is a schematic line and surface drawing depicting an embodiment of a molecularly imprinted bandage in accordance with the present invention the present invention.
Figure 14:
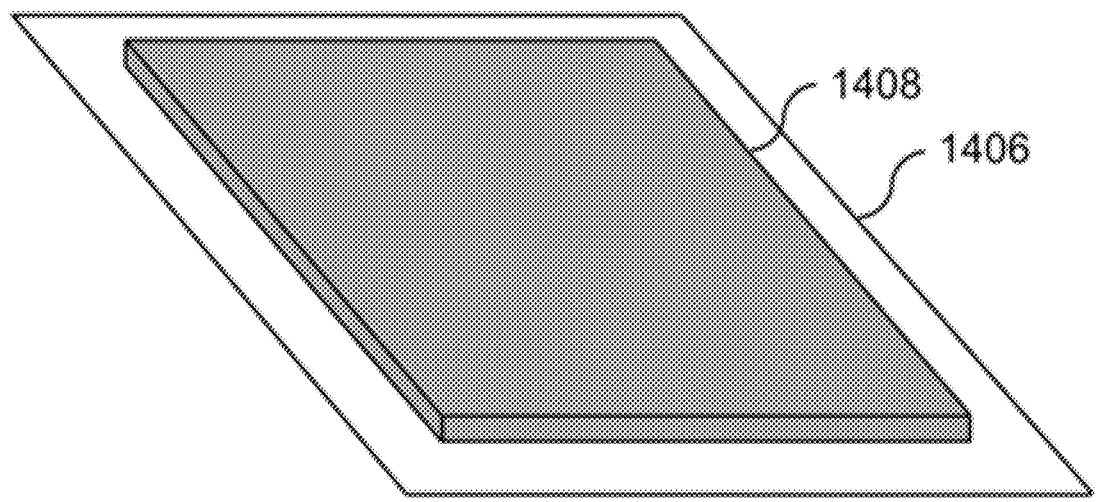

FIG. 14 depicts two embodiments of a molecularly imprinted bandage 1400 in accordance with the present invention and comprising a flexible molecular imprint polymer (MIP) layer 1402, an absorbent layer 1404, an external layer 1406, and molecular imprinted fibers 1408. In the first depicted embodiment the flexible MIP layer 1402 is in contact with the wound to reduce bleeding, facilitate healing, deaden pain, suppress infection, and/or provide other benefits. The MW layer 1402 sometimes comprises molecular imprints configured to catalyze and/or otherwise facilitate, without limitation, blood coagulation, would healing, pain suppression, inflammation control, and antibacterial action. The MW layer 1402 may be attached to the absorbent layer 1404 and is sometimes perforated or otherwise discontinuous to allow the absorbent layer 1404 to absorb fluids from the wound. In certain embodiments the absorbent layer 1404 is attached to the external layer, strip, or patch 1406 to protect the wound, MIP layer 1402, and absorbent layer 1404, and to hold the bandage 1400 onto the skin with adhesive or other attachment means around the boundary of the inside surface of the external layer 1410. The second embodiment incorporates molecular imprinted fibers 1408 into the absorbent layer 1404 thereby combining the biofunctionality of a molecular imprinted polymer with the absorbent layer 1408.

Figure 15:
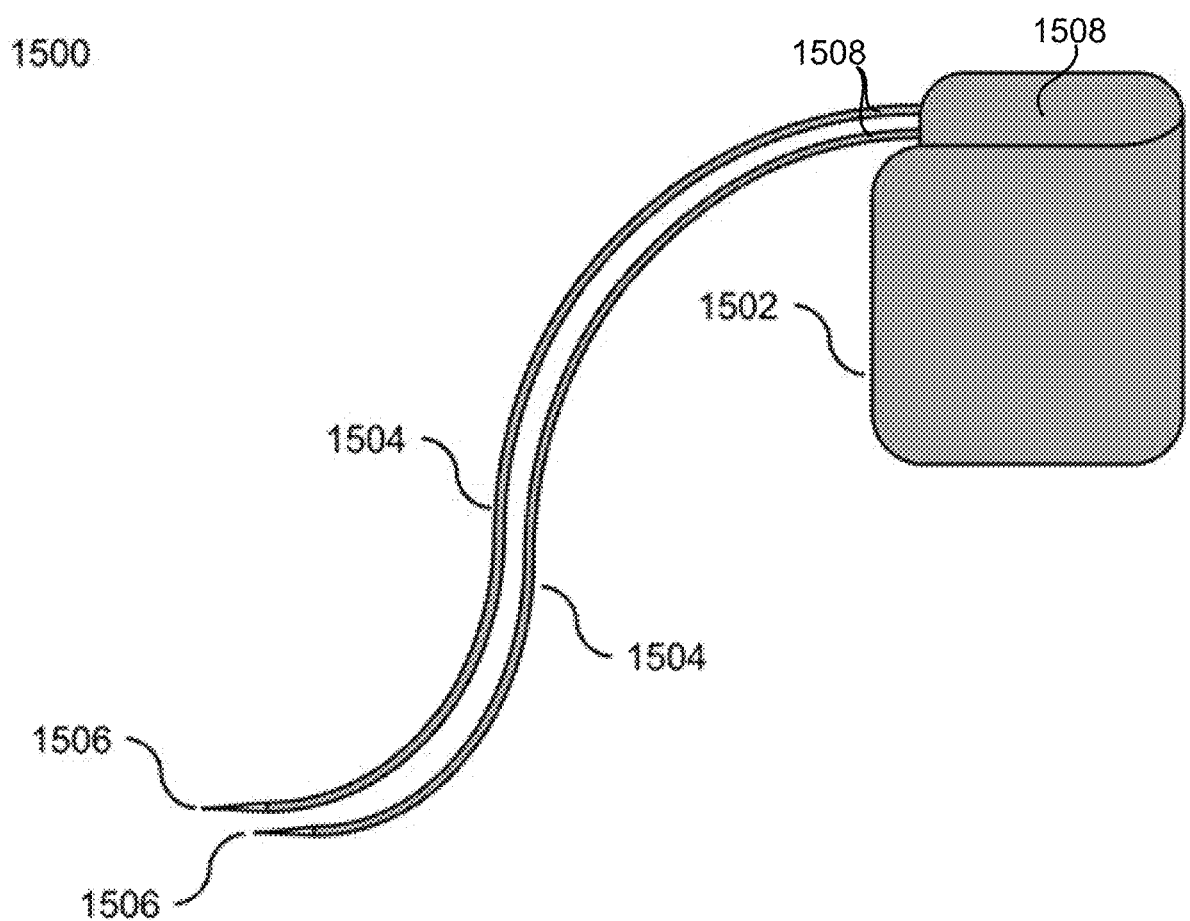
FIG. 15 is a schematic line and surface drawing depicting an embodiment of a molecularly imprinted pacemaker in accordance with the present invention.

FIG. 15 depicts an embodiment of a molecularly imprinted pacemaker 1500 in accordance with the present invention and comprising an implanted pacemaker 1502, lead wires 1504, lead wire tips 1506, and a molecular imprinted biofunctional layer 1508. As depicted the implanted pacemaker 1502 and the lead wires 1504 are coated with the molecular imprinted biofunctional layer 1508 which comprises molecular imprints configured to reduce the risk of blood clots, suppress infection, maintain healing, suppress inflammation, minimize immune responses against the foreign implanted device and material and/or provide other benefits. In various embodiments the lead wire tips 1506 are not coated to allow electrical contact with cardiac tissue.

Figure 16:
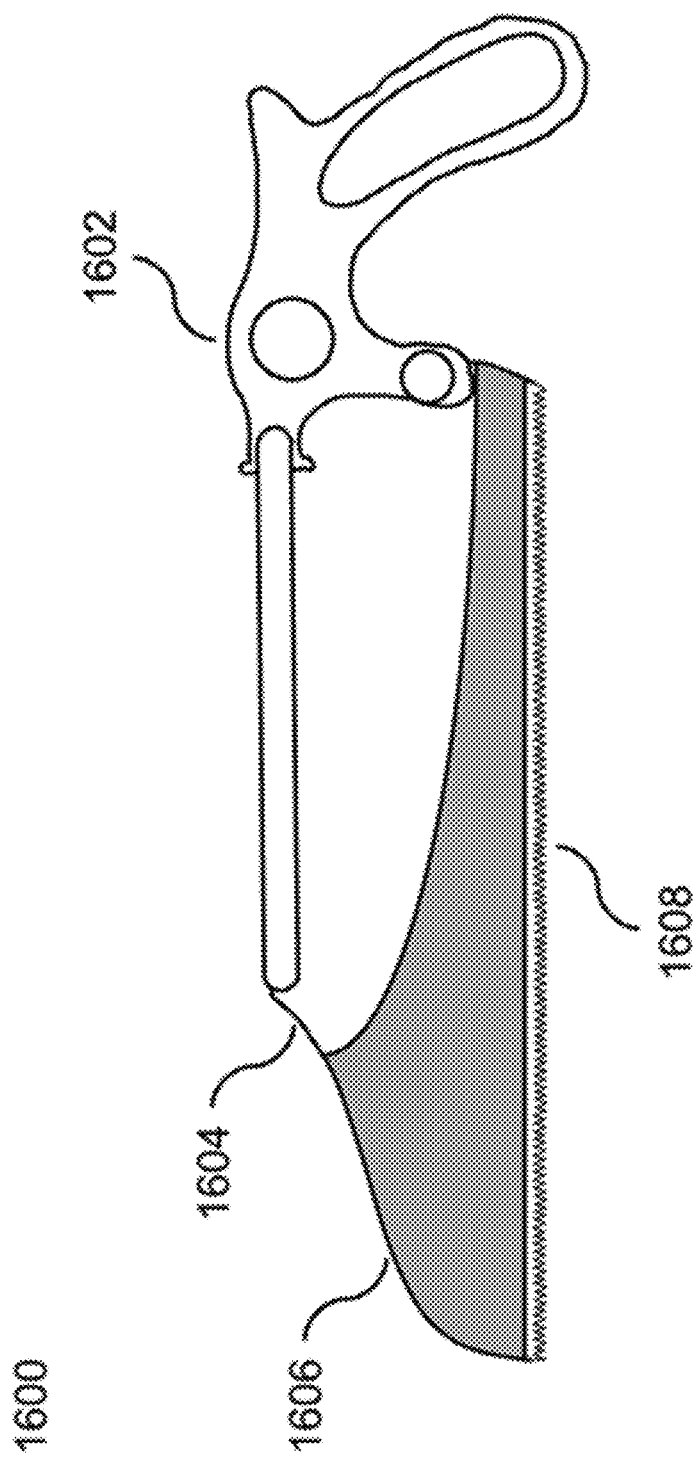
FIG. 16 is a schematic line and surface drawing depicting an embodiment of a molecularly imprinted bone saw in accordance with the present invention.

FIG. 16 depicts an embodiment of a molecularly imprinted bone saw 1600 in accordance with the present invention and comprising a handle 1602, stainless steel saw blade 1604, a molecular imprinted biofunctional layer 1606, and saw blade teeth 1608. In certain embodiments portions of the saw blade 1604 which come into contact with bone and tissue are coated with the molecular imprinted biofunctional layer 1606 which comprises molecular imprints configured to reduce bleeding, suppress infection, provide local pain relief, and/or to provide other beneficial effects. The saw blade teeth 1608 are sometimes not coated since the polymer coating of the molecular imprinted biofunctional layer 1606 might not hold a cutting edge and could wear away rapidly.

Figure 17:
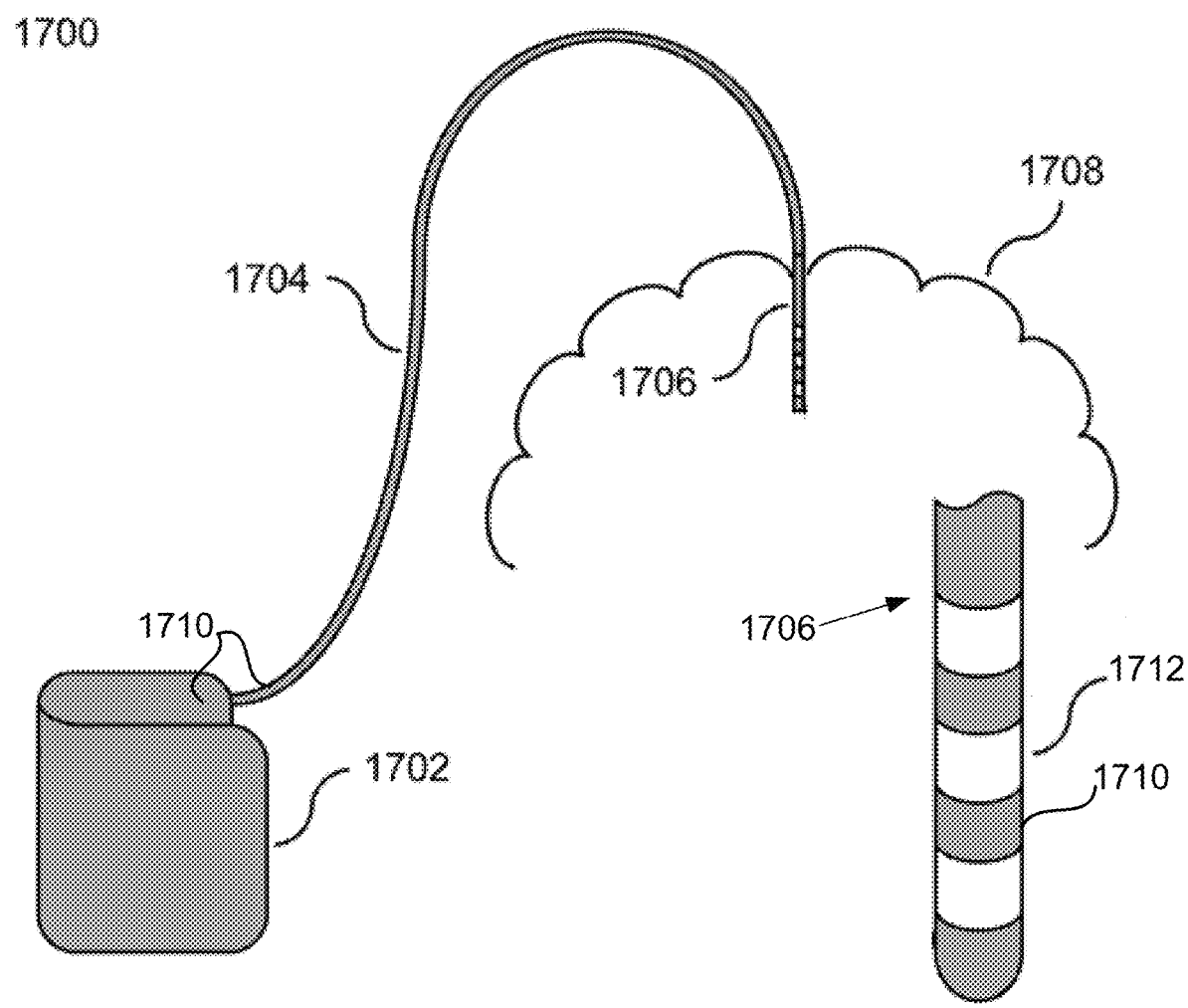
FIG. 17 is a schematic line and surface drawing depicting an embodiment of a molecularly imprinted intracranial brain electrode in accordance with the present invention.

FIG. 17 depicts an embodiment of a molecularly imprinted intracranial brain electrode 1700 for deep brain stimulation (DBS) in accordance with the present invention and comprising a pulse generator 1702, a lead 1704, a lead tip 1706, a molecular imprinted biofunctional layer 1710, and an electrode 1712. Also shown for illustration is a brain 1708. In some embodiments the pulse generator 1702 is implanted in the chest, and the pulse generator 1702 and lead 1704 are coated with the molecular imprinted biofunctional layer 1716 which comprises molecular imprints configured to reduce the risk of blood clots, suppress infection, minimize immune responses against the foreign implanted device and material, and/or provide other beneficial effects. The lead tip 1706 sometimes comprises an electrode 1712 and is implanted into the brain 1708. In some embodiments the lead tip is coated with the molecular imprinted biofunctional layer 1710. In some embodiments, as shown in a close-up of the lead tip 1706, the molecular imprinted biofunctional layer 1710 is deposited as discontinuous rings or other configurations to allow the electrode 1712 of the tip 1706 to come into contact with brain tissue.

Figure 18:
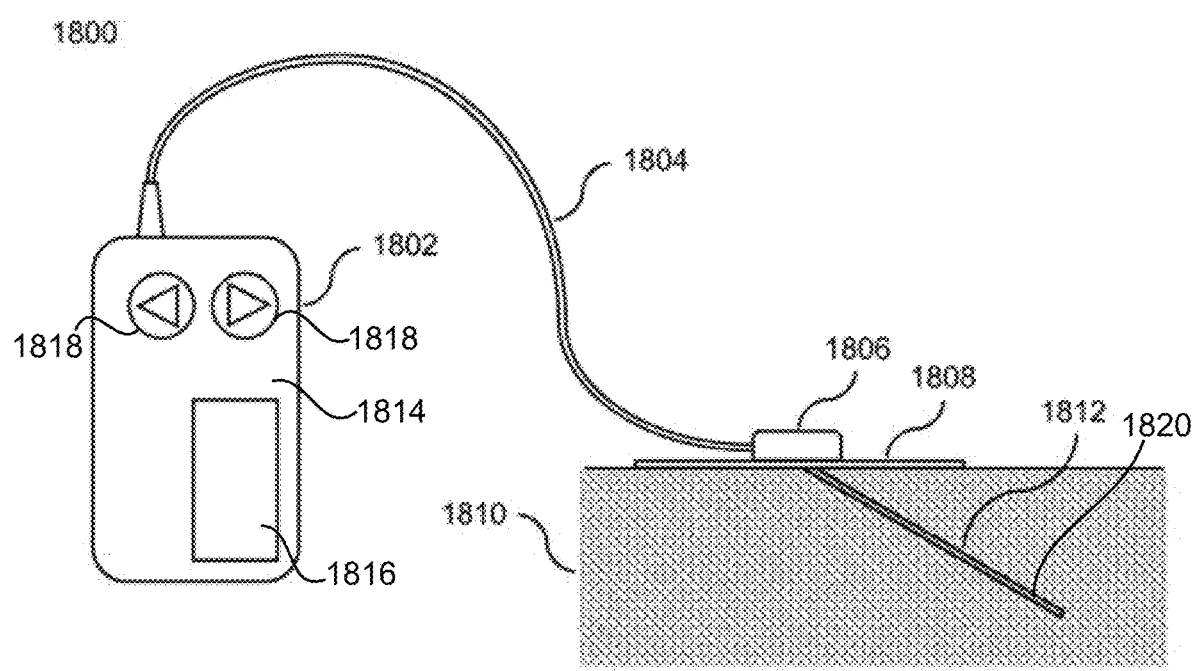
FIG. 18 is a schematic line and surface drawing depicting an embodiment of a molecularly imprinted insulin pump assembly in accordance with the present invention.

FIG. 18 depicts an embodiment of a molecularly imprinted insulin pump assembly 1800 in accordance with the present invention and comprising an externally worn insulin pump 1802, an external insulin reservoir 1814, a battery 1816, operating buttons 1818, tubing 1804, a connector 1806, an infusion set 1808, a cannula 1812 and a molecular imprint biofunctional layer 1820. Also shown for illustration is skin over fat tissue 1810. In certain embodiments the tubing 1804 delivers insulin to a connector 1806 on the infusion set 1808, which is adhesively attached to skin over fat tissue 1810. The cannula 1812 may be attached to the connector 1806 and infusion set 1808, and deliver insulin into the fat tissue. The cannula 1812 is coated with the molecular imprinted biofunctional layer 1820 which comprises molecular imprints configured to reduce the risk of blood clots, suppress infection, minimize immune responses against the cannula, and/or provide additional beneficial effects.

EXAMPLES

Example 1: The Manufacture of a Molecular Imprinted Surgical Scalpel that Reduces Bleeding A procedure for creating molecular imprints on a scalpel blade comprises the following steps. (1) Molecules of a specific blood protein required for blood coagulation (for example, thrombin) are absorbed onto the surface of a thin mica sheet. (2) A buffer is added to neutralize the pH of the mica-protein surface. (3) The mica sheet-buffer solution is heated and subsequently cooled. (4) The mica sheet is rinsed with deionized water and spin cast with a disaccharide to allow coating.

The hydroxyl groups on the disaccharide molecules, combined with the surface polar residues of the protein molecules, facilitate the formation of hydrogen bonds during dehydration. Hydrogen bonds are vital for molecular recognition in biological signaling. The disaccharide coating also protects the protein molecules from dehydration and damage during the following plasma deposition process, thus preserving the fidelity of the imprinted cavities.

(5) A thin fluoropolymer film is deposited onto the mica surface using radio-frequency glow-discharge plasma deposition and hexafluoropropylene. (6) The fluoropolymer film is glued to a stainless steel blade of a scalpel with epoxy. The scalpel blade provides mechanical support for the fluoropolymer film. (7) The mica sheet is peeled from the blade-supported fluoropolymer film. (8) The protein molecules are removed from the fluoropolymer film using a solvent wash, leaving behind molecular imprints of the protein.

The above procedure may be utilized to molecularly imprint a set of diverse proteins onto a scalpel blade in a specific spatial pattern, as shown in FIG. 2 to replicate the blood coagulation cascade of FIG. 13 as the scalpel slices through tissue. Non-limiting examples of proteins that could be used for each molecular-imprinted polymer region on the scalpel blade are the following. (1) On region 1 closest to the blade edge (202), molecules are imprinted to initiate the cascade pathway through vasoconstriction and platelet adhesion (creation of a platelet obstruction). These molecules include endothelin plus associated enzymes, thromboxane A2, and Von Willebrand factor. (2) On region 2 (204), molecules are imprinted to aid in the extrinsic pathway, as shown in FIG. 13 (1300, 1316, 1318), including thromboplastin and lipoprotein. (3) On region 3 (206), molecules are imprinted to accelerate the common pathway, including factors IX (1310) and IXa (1312) from the intrinsic pathway, factors VIII (1314) and VIIIa, and factors V and Va (1322). (4) On region 4 (208), molecules are imprinted for the direct activation of thrombin. These include PAR-1, PAR-4, and GP Ib-alpha (1324), and prothrombin (1326).

In the event that certain molecular imprints do not function similarly to their protein molecule counterparts, molecular "outprints" can be created by a stamping method that first creates the molecular imprints on nanoparticles. A polymer film is then stamped with these molecularly imprinted nanoparticles, creating a negative image of the molecular imprint, or an outprint. These molecular outprints will have the same positive shape as the original molecule, and may, therefore, have a functionality more similar to the original molecule.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A biofunctional molecular imprint apparatus, the apparatus comprising:
   a supportive structure of a surgical or medical apparatus the supportive structure comprising at least one of a scalpel, a scissor, a needle, a clamp, a cutting tool, a forceps, a drill, and a bone saw;
   a surface material that receives and retains a molecular imprint and that is positioned to contact a body tissue or other substance during use; and
   a molecular imprint of a bioactive molecule, an imprinted cavity of the bioactive molecule configured to interact with a molecule specific to at least one of blood coagulation, tissue damage, pain, immune response, inflammation, infection, healing, tissue regeneration, cell adhesion, the formation of extracellular matrix, tumorigenesis, angiogenesis, bacterial growth, and side effects.

2. The apparatus of claim 1, wherein the surface material comprises a polymer film.

3. The apparatus of claim 1, wherein the bioactive molecule comprises at least one of fibrinogen, fibronectin, PAR-1, PAR-4, ephedrine, a VEGF inhibitor, and an HER2-inhibitor.

4. The apparatus of claim 1, wherein the supportive structure comprises at least one of titanium, stainless steel, ceramic, plastic, carbon polyethylene, cobalt chromium alloys, ceramic, tantalum, zirconium alloy, oxinium alloy, and other biocompatible material.

5. The apparatus of claim 1, wherein the supportive structure comprises a medical device.

6. The apparatus of claim 1, wherein the needle comprises at least one of a hypodermic needle, a biopsy needle, and an intravenous needle.

7. The apparatus of claim 1, wherein the surface material further comprises a plurality of zones that contact the tissue at different stages of at least one of cutting, piercing, retaining, or penetrating the tissue and the molecular imprint comprises one or more molecularly distinct imprinted cavities arrayed within the zones.

8. The apparatus of claim 1 wherein at least one of the supportive structure and the surface material comprises a transducer comprising an interdigital electrode and other device.

9. The apparatus of claim 1 wherein at least one of the supportive structure and the surface material further comprises at least one of a semiconductor, a nanoparticle quantum dot, a nano-island, and a wire.

10. The apparatus of claim 1, wherein at least one of the supportive structure and the molecular imprint is designed for at least one of use in a specific type of surgery and a treatment of a specific disease.

11. The apparatus of claim 1, wherein the molecular imprint is customized to a specific patient or set of patients.

12. The apparatus of claim 9 wherein the nanoparticle quantum dot, nano-island, or wire produces an electron wave function configuration that dynamically reconfigures the electron charge distribution within the molecular imprint, enabling tuning of the imprinted cavity.

13. The apparatus of claim 9 further comprising an insulating material separating the supportive structure from the polymer film and the molecular imprints.

14. The apparatus of claim 1, further comprising at least one of a piezoelectric element and a semiconductor that generates at least one of ultrasonic and light waves.

15. The apparatus of claim 14, further comprising at least one of an acoustic waveguide, an optical fiber, ultrasonic transducer, and a laser that mechanically agitates a protein molecule and induces its interaction with the molecular imprint.

16. The apparatus of claim 1 comprising a molecular imprint specific to at least one of inhibiting the transfer of pathogens on the apparatus surfaces, and sensing the presence of at least one of tissue specific and pathogen biomarkers.

17. The apparatus of claim 1 comprising a cutting tool wherein during a cutting process the molecular imprint at least one of enhances a cross-link density of a soft polymer on a cut surface, changes the polarity of the cut surface to render the surface hydrophobic or hydrophilic, and otherwise alters the cut surface.

* * * * *